United States Patent [19]
Yezrielev et al.

[11] Patent Number: 5,817,722
[45] Date of Patent: Oct. 6, 1998

[54] LOW VISCOSITY, HIGH SOLIDS POLYESTERDIOLS AND COMPOSITIONS CONTAINING SAME

[75] Inventors: Albert Ilya Yezrielev, Houston, Tex.; Konstantinos R. Rigopoulos, Baton Rouge, La.; Richard William Ryan, Kingwood; Karen K. Kuo, Seabrook, both of Tex.; George Andrew Knudsen, Scotch Plains, N.J.

[73] Assignee: Exxon Chemical Patents Inc., Houston, Tex.

[21] Appl. No.: 617,709

[22] Filed: Apr. 1, 1996

Related U.S. Application Data

[60] Provisional application No. 60/004,977 Oct. 10, 1995.

[51] Int. Cl.$^6$ .............................. C08F 20/00; C08G 63/16
[52] U.S. Cl. ...................... 525/441; 528/302; 528/303; 528/308; 525/437; 525/442; 525/443
[58] Field of Search ................................. 528/302, 303, 528/308; 525/437, 441, 442, 443

[56] References Cited

U.S. PATENT DOCUMENTS

| | | | |
|---|---|---|---|
| 3,079,350 | 2/1963 | Bernstein . | |
| 3,852,375 | 12/1974 | Biethan et al. | 260/850 |
| 3,888,908 | 6/1975 | Cross et al. | 260/475 |
| 3,994,851 | 11/1976 | Chang | 260/29.4 |
| 4,018,815 | 4/1977 | Vogt et al. | 260/485 |
| 4,104,240 | 8/1978 | Buter | 260/39 |
| 4,243,705 | 1/1981 | Yapp et al. | 427/386 |
| 4,294,738 | 10/1981 | Beresniewicz | 260/29.4 |
| 4,352,924 | 10/1982 | Wooten | 528/302 |
| 4,442,270 | 4/1984 | Passmore | 525/440 |
| 4,540,771 | 9/1985 | Ambrose et al. | 528/272 |
| 4,616,054 | 10/1986 | Olson | 524/317 |
| 4,888,441 | 12/1989 | Calbo, Jr. et al. | 560/198 |
| 4,922,002 | 5/1990 | Calbo, Jr. et al. | 560/193 |
| 4,922,992 | 5/1990 | Calbo, Jr. et al. . | |
| 5,587,428 | 12/1996 | Jones et al. | 525/165 |

FOREIGN PATENT DOCUMENTS

| | | |
|---|---|---|
| EP-A-86085 | 8/1983 | European Pat. Off. . |
| WO-A-9519997 | 7/1995 | WIPO . |

OTHER PUBLICATIONS

SRI International, Polyols for Making Polyurethanes, Supplement A; by Yen–Chen Yen contributions by Tung–Sheng Tsao; Report No. 45A, pp. 203–208, May 1982.
P. Flory, JACS, V62, p. 1057 (1940).
Olson, M.R., Larson, J.M., Jones, F.N., J. Coat. Technol., 55, (699) p. 45, 1983.
Blank, W.J., J. Coat. Technol. 60, (764), p. 43, 1988.
Blank, "Polyurethane Oligomers for Water–Borne and High Solids Coatings," Jornal of Coatings Technology, vol. 60, No. 764, Sep. 1988, p. 43.
Flory, "Viscosities of Linear Polyesters, etc.", JACS, vol. 62, p. 1057, May 1940.
Olson et al., "Water Extendable High Solids Enamels", Journal of Coatings Technology, vol. 55, No. 699, Apr. 1983, p. 45.

Primary Examiner—Samuel A. Acquah
Attorney, Agent, or Firm—John F. Hunt

[57] ABSTRACT

Polyesterdiols having low viscosities of less than 3500 cps, high content of non-volatile matter in excess of 96 wt %, and narrow molecular weight distribution of less than about 1.4 are prepared by esterification of one or more aliphatic dicarboxylic acids or ester derivatives thereof using at least a 1.5 molar excess of one or more aliphatic diols until an acid number of less than 20 is achieved, and stripping excess diol from the polyesterdiol reaction product. Where esterification catalyst is used, catalyst is substantially removed prior to stripping excess unreacted diol from polyesterdiol reaction product. The polyesterdiols so produced are useful as (i) curable components in thermosettable resin compositions, particularly compositions essentially free of volatile organic solvent and also containing a crosslinking agent and a reactive hardening agent: and/or (ii) useful as coatings, paints and adhesives, providing coatings with very low content of volatile organic compounds.

84 Claims, No Drawings

LOW VISCOSITY, HIGH SOLIDS POLYESTERDIOLS AND COMPOSITIONS CONTAINING SAME

BACKGROUND OF THE INVENTION

This application is a continuation-in-part of Provisional application Ser. No. (60/004,977) filed in the U.S. Patent and Trademark Office on Oct. 10, 1995, the complete disclosure of which is incorporated herein by reference.

1. Field of the Invention

This invention relates to low viscosity, high solids content polyesterdiols, their use in high solids content, curable resin compositions and curable coating compositions containing these polyesterdiols which are essentially free of volatile organic compounds.

2. Description of Related Art

Polyester diols having a relatively low viscosity and a relatively high content of non-volatile material (NVM) are known in the art. These materials are useful as components in curable formulations such as coatings, paints or adhesives and as precursors in the preparation of polyurethanes.

These polyester diols are generally prepared by reacting $C_4$ to $C_{20}$ aliphatic, cycloaliphatic, or aromatic dibasic acids or acid derivatives (or mixtures thereof) under esterification conditions with a molar excess of one or a mixture of aliphatic polyols, to produce polyester diols having the general structure:

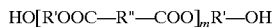

HO[R'OOC—R"—COO]$_n$R'—OH where R' is the organic residue of an aliphatic polyol and R" is the organic residue of a dibasic acid or acid derivative. Polyester diols, also referred to as polyester di(poly)ols are telechelic oligomers which are especially useful as binder components in curable resin systems, as stated above. Because of concerns in the paint and coating industry with respect to reduction of solvent (volatile organic compound or VOC) emissions into the atmosphere during baking of the resin composition, there is a considerable interest in providing reactive polyesterdiol components which have both very low viscosity and very low VOC content. The lower the polyesterdiol viscosity, the less solvent will be required to be added to the resin composition in order to produce a coating or paint which is readily sprayable on substrates. However, even in the case of low molecular weight polyesterdiols, reduced solvent content results in a coating composition too viscous to be applied by spray at low temperatures. For example, U.S. Pat. No. 4,243,705 teaches spray application of such coatings at temperature up to about 250° F.

U.S. Pat. No. 3,994,851 teaches high solids coating compositions prepared from a mixture of an ester-containing polyol having a molecular weight of less than about 850 and an amine-aldehyde crosslinking agent. Although the reference describes the preparation of ester-containing polyols having a viscosity of as little as 1.4 to 12.9 poises (about 140 to 1290 cps), these viscosities appear to be based on the ester-containing polyol "as synthesized", which would contain a considerable amount of unreacted polyol diluent. The reference does not disclose that unreacted polyol is removed. Thus, where the reference describes high solids coatings which may have a solids content of up to 100%, consideration of quantities of unreacted polyol present in the ester-containing polyol is evidently not taken into account.

In many cases, the term NVM means that the polyester does not contain any added solvent and does not mean 100% NVM as defined by ASTM D2369-90. Sometimes it is referred as "Theoretical" or "Calculated" NVM. For example, Cargill (now McWhorter) commercial 100% NVM polyesters 57-5763, 57-5879 and 57-5880 have NVM measured according ASTM D2369-90 of about 91%, 72% and 74% respectively and, therefore, contain significant VOC which is primarily unreacted diol. U.S. Pat. No. 3,852,375 discloses the preparation of curable varnishes and enamels comprising a mixture of an ester diol having a molecular weight of from about 200–600 derived from aliphatic diols and a mixture of aliphatic and aromatic or cycloaliphatic diacids, and an aminoplast crosslinking resin. In this patent, the authors describe measures to keep an excess of diol from the start to the end of the synthesis process without any attempt to remove excess of diol.

U.S. Pat. No. 4,104,240 describes the preparation of low molecular weight and narrow molecular weight distribution polyester diols. The authors teach reacting excess diol (2–4 moles) per 1 mole of diacid in presence of catalyst, followed by vacuum distillation at 90° C. This low temperature for distillation was chosen to achieve essentially non-reacting conditions and avoid transesterification during distillation. The authors do not provide data relating to NVM or viscosities of these products. It should be also recognized that 90° C. is not a commercially viable temperature to achieve quantitative distillation of high boiling temperature diols from polyesterdiol due to excessively long processing times.

U.S. Pat. No. 4,104,240 also discloses curable pigmented coating compositions containing an amino or polyisocyanate curing agent and a mixture of two different ester diols, one of which is the esterification product of a divalent alcohol and a cycloaliphatic and/or aromatic dicarboxylic acid (molecular weight 254–2000) and the other of which is the esterification product of a divalent alcohol and an aliphatic dicarboxylic acid (molecular weight 178–2000). The pigmented, cured compositions are said to have improved flexibility and hardness.

Similar processes are disclosed in U.S. Pat. No. 4,888,441 and related U.S. Pat. No. 4,922,002. In these disclosures, a dibasic ester of a dicarboxylic acid is reacted with an excess of a polyhydric alcohol and in the presence of an esterification catalyst to produce polyester polyols, followed by stripping excess unreacted polyhydric alcohol using a wiped film evaporator at temperatures of 150°–225° C. and 0.05–200 torr, and cooling the resultant product to prevent further reaction. The use of a wiped film evaporator reduces high temperature residence time during distillation and therefore substantially reduces transesterification effect on the structure and viscosity of the polyesterdiol. The products are characterized as containing less than about 4% by weight of polyhydric alcohol and have viscosities of above 3700 cps as made in the examples.

A method equivalent to the process disclosed in U.S. Pat. No. 4,104,240 is also disclosed and claimed in U.S. Pat. No. 4,540,771. However, despite listing many commercially available monomers for polyester diols, the authors demonstrate their invention only using polyesterdiols of cycloaliphatic or aromatic diacids which, by their chemical structure, provide polyesterdiols with significant resistance to transesterification. Polyesterdiols having a solids content in excess of 95% are disclosed in some of the examples, but all of these materials have viscosities in excess of 60 poises (6000 cps).

It is known in the literature (P. Flory, JACS, V62, p. 1057 (1940)), that polyesters based on aliphatic dicarboxylic acids are prone to transesterification even in the absence of a catalyst used in their synthesis, and at a temperature as low as 109° C. Therefore, to prevent the negative effect of transesterification in the preparation and stripping of very low molecular weight polyesters, researchers resorted to very low distillation temperature (U.S. Pat. No. 4,104,240), very short distillation time (U.S. Pat. No. 4,922,002) or simply avoided the use of aliphatic diacids (U.S. Pat. No. 4,540,771).

Transesterification of the polyesterdiol during stripping can lead to a product having an increased molecular weight, a broader molecular weight distribution and an increased viscosity of the stripped polyesterdiol. In addition, transesterification is accompanied by the development of monomeric diol as a transesterification by-product which is counterproductive to achieving a product having a high NVM content.

Thus, the goal to achieve aliphatic polyesterdiols of low viscosity and having a very low content of residual diol using post-synthesis stripping techniques is counteracted by the problem of viscosity and molecular weight increase of the polyesterdiol which takes place as a consequence of the stripping step. Viscosities of polyesterdiols depend on their monomer compositions and, even at the same molecular weight and molecular weight distribution, viscosities can be significantly different.

Therefore, an important goal of the invention is to provide a definition of the optimal molecular weight distribution providing optimal viscosity for any particular polyesterdiol comprising aliphatic diacid moieties, technique to measure their molecular weight and molecular weight distribution, industrially viable technique to produce such polyesterdiols and the polyesterdiols themselves. High purity polyesterdiols produced according to the process of the present invention are among the goals of the present invention.

Accordingly, the present invention provides polyesterdiol materials having both a very low viscosity below 3500 cps and a very high content of non-volatile material in excess of 96 wt % and up to about 100 wt %.

The invention also provides processes for the production of aliphatic polyester diols wherein transesterification reactions encountered during heat stripping of unreacted diol are markedly reduced.

The invention provides crosslinkable compositions providing improved properties and lower VOC comprising the polyesterdiols of the present invention.

The major function of solvents in coating composition is to reduce viscosity to the level necessary for applicability by techniques developed for liquid coating compositions, especially for spray.

U.S. Pat. No. 4,243,705 described significant increase in temperature of coating compositions (up to 250° F.)—hot spray to reduce viscosity without further increase of solvent content in coating compositions. This method still has some limitations—high temperatures significantly increase fire hazard; at high temperatures curable coating compositions become unstable due to the crosslinking process.

Another interesting approach is substitution of part of the VOC generating solvent with VOC free water (Olson, M. R., Larson J. M., Jones, F. N., J. Coat Technol. 55(699) p. 45,1983; Blank, W. J., J. Coat. Technol. 60(764), p. 43, 1988; M. R. Olson, U.S. Pat. No. 4,616,054 Beresniewicz, A. U.S. Pat. No. 4,294,738). In this approach many water miscible solvents, especially glycols and their derivatives significantly increase compatibility of poly(oligo)meric components with water allowing the system to imbibe more water and correspondingly to achieve more reduction in viscosity. However, the water-miscible glycols and their derivatives are VOC-generating solvents and reduction in viscosity is limited by solubility of water in the poly(oligo)

mer-glycol (glycol derivative) mixture and increases with the increase of the level of the VOC-generating components.

Nevertheless, despite numerous efforts, industry still does not have the solvent-free curable compositions with low viscosity applicable by techniques developed for liquid coating compositions.

The invention provides liquid, curable, polyesterdiol-containing coating compositions which are essentially free of VOC-generating solvents, including unreacted diols, and which can be applied to substrates at low temperature using conventional application methods.

SUMMARY OF THE INVENTION

The present invention provides a polyesterdiol composition having the average structure:

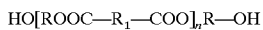

$$HO[ROOC—R_1—COO]_nR—OH$$

wherein R is a moiety derived from one or a mixture of aliphatic diols having from 2 to 12 carbon atoms, $R_1$ is a moiety derived from one or a mixture of aliphatic dicarboxylic acids having from 4 to 36 carbon atoms or a mixture of said aliphatic dicarboxylic acid with up to 50 mol % of an aromatic and/or cycloaliphatic dicarboxylic acid having from 8 to 12 carbon atoms and n a number averaging from greater than 1 to less than 3, said polyester diol characterized by a Brookfield viscosity of less than 3500 cps at 25° C., a non-volatile material content in excess of about 96 wt %, and a polydispersity of less than about 1.4. Preferably n has an average value of about 2.0 or less.

The invention also provides a process for producing a polyester diol composition having a viscosity of less than 3500 cps at 25° C., a non-volatile material content in excess of about 96 wt % and a polydispersity of less than 1.4 comprising: (a) heating under esterification conditions and in the absence of added esterification catalyst a mixture comprising: (i) at least one aliphatic dicarboxylic acid or acid anhydride thereof or a mixture of an aliphatic dicarboxylic acid or acid anhydride thereof with up to 50 mol % of an aromatic or cycloaliphatic dicarboxylic acid or acid anhydride thereof, and (ii) at least one aliphatic diol, said diol present at a molar ratio of diol to dicarboxylic acid of at least 1.5 to 1; (b) continuing said heating until a polyesterdiol having an acid number of less than 20 is obtained; and (c) stripping said polyesterdiol by heating at a temperature of less than about 230° C., optionally under vacuum, until a polyesterdiol having an NVM content in excess of 96 wt % is obtained. The diol composition so produced may conveniently be essentially free of catalytic impurities.

In a further embodiment, the invention provides a process for producing a polyesterdiol composition having a viscosity of less than 3500 cps at 25° C., a non-volatile material content in excess of about 96 wt % and a polydispersity of less than 1.4 comprising: (a) heating under esterification conditions and in the presence of catalytic quantities of esterification catalyst a mixture comprising: (i) (A) at least one aliphatic dicarboxylic acid or anhydride thereof or lower alkyl diester thereof, or (B) a mixture of aliphatic dicarboxylic acid or anhydride thereof or lower alkyl diester thereof and up to 50 mol % of an aromatic or cycloaliphatic dicarboxylic acid or anhydride thereof or lower alkyl diester thereof and (ii) at least one aliphatic diol, said diol present at a molar ratio of diol to dicarboxylic acid or derivative thereof of at least 1.5 to 1; (b) continuing said heating until said esterification reaction is substantially complete and an acid number of less than 20 is achieved, (c) removing said esterification catalyst from the product of step (b) such that the product contains less than catalytic quantities of said catalyst; and (d) stripping the product of step (c) at a temperature of less than about 230° C., optionally under vacuum, until a polyesterdiol having an NVM content in excess of 96 wt % is obtained.

The invention is also a crosslinkable coating composition comprising a mixture of:
  a. one or a mixture of a poly(oligo)meric hydroxy-functional polymer components selected from the group consisting of di(poly)esters, alkyd resins, acrylic resins, polyether polymers, polycarbonate resins, and poly(oligo)mers which contain a combination of two or more of ester, ether, carbonate, acrylic and alkyd moieties in their structure, said polymeric component further characterized as a having a number average molecular weight within the range of about 250 to about 20,000; and
  b. from about 2 to about 95 wt % of the polyesterdiol composition above.

The invention is also a composition useful as a reactive diluent and hardening agent for hydroxy functional poly(oligo)mer and amino-crosslinker compositions, comprising:
  a. 10–95 wt. % of the polyesterdiol above having a Mn less than 700; and
  b. 5–90 wt. % of a hardening agent compatible with said polyesterdiol and having a Mn less than 800;

The invention is also a crosslinkable coating composition which is essentially free of volatile organic solvent and which has a Brookfield viscosity of less than 3,000 at 25° C., comprising a mixture of:
  a) a polyesterdiol having the average structure:

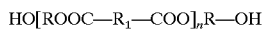
HO[ROOC—R$_1$—COO]$_n$R—OH wherein R is a moiety derived from one or a mixture of aliphatic diols having from 2 to 12 carbon atoms, R$_1$ is a moiety derived from one or a mixture of aliphatic dicarboxylic acids having from 4 to 36 carbon atoms or a mixture of said aliphatic dicarboxylic acid with up to 50 mol % of an aromatic and/or cycloaliphatic dicarboxylic acid having from 8 to 12 carbon atoms and n a number averaging from greater than 1 to less than 3, said polyester diol characterized by a Brookfield viscosity of less than 3500 cps at 25° C., a non-volatile material content in excess of about 96 wt %, a polydispersity of less than about 1.4 and a number average molecular weight of less than about 700;
  b) an amino crosslinking agent, present in said composition in an amount sufficient to crosslink said composition; and
  c) 0 up to about 50 wt % of a hardening agent containing functional groups reactive with said amino crosslinking agent and which is compatible with said polyesterdiol, said hardening agent having a number average molecular weight of less than about 800.

The invention is also, in a catalyzed coating process to achieve a coating having a first hardness and meeting EPA-measured VOC, the improvement comprising:
  a. using on a substrate, a coating composition essentially free of volatile organic solvent and unreacted diol; and
  b. (i) increasing the baking time or temperature or both; or (ii) reducing the catalyst level or activity; or (iii) both (i) and (ii); and
  c. (i) producing a coating having hardness higher than said first hardness while meeting or reducing EPA-measured VOC; or (ii) reducing EPA-measured VOC while obtaining or exceeding said first hardness.

The polyesterdiols produced in accordance with the present invention are essentially free of catalytic impurities and are particularly suitable for use as reactive binder components in curable coating formulations or as reactive diluents in such formulations, capable of participating in binder crosslinking reactions, thereby providing low viscosity formulations with an extremely high NVM content.

In particular, the present invention also provides for low VOC content curable coating compositions comprising a low viscosity polyesterdiol as described above, an effective amount of an amino crosslinking agent and, optionally, also containing an effective amount, preferably up to about 50 wt % of a hardening agent which has functional groups reactive with the amino crosslinking agent and which is compatible with the polyesterdiol component of the composition, and optionally a pigment or pigment composition or pigment filler composition. Preferred compositions, which can be made to be essentially free of VOC-generating solvents can be prepared utilizing a polyesterdiol component as described above but having an Mn of less than 700, a hardening agent having an Mn of less than 800 and an amino crosslinking agent, preferably a methylol (alkoxymethyl) amino crosslinking agent, present in said composition in an amount sufficient to crosslink the composition.

BRIEF DESCRIPTION OF THE DRAWINGS

FIG. 1 shows a chromatogram and calibration curve relating to the GPC process used for determining molecular weight in accordance with this invention.

FIG. 2 is a plot showing GPC data for propylene glycol adipate produced in accordance with Example 13 prior to and subsequent to stripping of excess diol according to Examples 11 and 12.

FIG. 3 is a plot showing GPC data for propylene glycol adipate produced in accordance with Example 14 prior to and subsequent to stripping of excess diol according to Examples 11 and 12.

DETAILED DESCRIPTION OF THE INVENTION

The invention is based on the unexpected discovery that, when polyesterdiols are prepared from a monomer mixture comprising one or more aliphatic dicarboxylic acids or anhydrides and one or more aliphatic diols in a molar excess of the diol to total content of diacid of at least 1.5 times in the absence of catalyst, and the reaction continued until a low enough acid number is achieved, the polyesterdiol mixture with the excess of unreacted diol formed during the reaction acquires an exceptional resistance to transesterification and the excess of diol can be distilled out of the mixture, even at temperatures as high as reaction temperatures, without substantial negative effect of the distillation on molecular weight distribution and viscosity of the polyesterdiol.

This exceptional resistance to transesterification allows distillation of more than 50%, preferably more than 75% and more preferably more than 90% of the unreacted diol from the polyesterdiols comprising ester groups derived from aliphatic diacids without any substantial transesterification taking place. As a result of this discovery, stable polyesterdiols can be prepared with a highly desirable combination of properties, i.e., a very low viscosity and very high NVM, in most cases in the range of 99–100%. The viscosities achievable in accordance with the present invention are often 2–3 times less than the viscosity of corresponding low molecular weight commercial products or products described in the literature. These new materials are effective components for use in compositions targeted for further reduction of VOC in different formulations.

As indicated above, the polyesterdiols of the present invention may be prepared by the esterification reaction of at least one aliphatic dicarboxylic acid or anhydride derivative thereof and at least 1.5 times molar excess of at least one aliphatic diol. The reaction is driven until the acid number of the polyesterdiol reaction product is less than 20, preferably less than 10, more preferably less than 5 and most preferably less than 3.

The results were further generalized to the production of polyesterdiols in presence of a catalyst. When the diacid components are used in the diacid or anhydride form, or in the form of lower dialkyl ester, or a combination thereof, the reaction should be driven to completion by achieving an acid number of less than 20, preferably less than 10, more preferably less than 5 and most preferably less than 3, and, in case of the dialkyl ester, the liberation of essentially all of the monoalcohol byproduct. Residual catalyst present in the resulting polyesterdiol is then at least partially removed such that less than catalytic quantities of catalyst remain. Equimolar quantities of the diol and lower dialkyl ester can be substituted with a lactone.

The resulting aliphatic polyesterdiol produced by either method is extremely resistant to further transesterification reactions such that most or all of the excess unreacted diol can be heat stripped from the polyesterdiol without significant further ester exchange reactions taking place. The resulting products accordingly have a low viscosity of less than 3500 cps at 25° C., an NVM content of greater than 96 wt %, a polydispersity (Mw/Mn) of less than 1.4 and a number average molecular weight (Mn) in the range of from about 250 to 1,000.

The dicarboxylic acid component used to prepare the polyester diols includes aliphatic dicarboxylic acids or a mixture of aliphatic and up to 50 mol % cycloaliphatic and/or aromatic dicarboxylic acids, having from 4 to about 36 carbon atoms, more preferably from about 4 to 10 carbon atoms. The carboxyl groups may be present in the form of anhydride groups, lactone groups, or equivalent ester forming derivatives such as the $C_1$ to $C_4$ dialkyl ester. Suitable aliphatic acids include adipic acid, succinic acid, glutaric acid, fumaric acid, maleic acid, azelaic acid, sebasic acid, $C_{38}$ dimer acid, caprolactone, propiolactone, substituted maleic and fumaric acids such as citraconic, chloromaleic, mesaconic, and substituted succinic acids such as aconitic and itaconic, and mixtures thereof. A combination of aromatic and aliphatic dicarboxylic acids or a combination of cycloaliphatic and aliphatic dicarboxylic acids or combinations of all three types may also be used. Suitable aromatic acids are phthalic acid, isophthalic acid, terephthalic acid, their respective anhydrides and like materials. However, where polyester diols having very low viscosity are desired, the most preferred acids used for the purposes of this invention consist of linear saturated aliphatic dicarboxylic acids having from 4 to 10 carbon atoms such as succinic, glutaric, adipic, and similar materials, or mixtures of such acids with less than 25 mol %, preferably less than 10 mol % of aromatic and/or cycloaliphatic dicarboxylic acids. Up to about 10 mole % of the diacid component may also be replaced with one or more tricarboxylic acids.

Diols used in preparing the polyesterdiols are $C_2$ to $C_{12}$ diols with primary, primary-secondary or secondary hydroxyls. Tertiary hydroxyls should be avoided due to their slow reaction in the esterification process and instability under reaction conditions. Examples of suitable diols are ethylene glycol; propanediols 1,2 and 1,3; butanediols 1,2, 1,3 and 1,4; 2-methyl propanediol 1,3; neopentyl glycol; hexanediols 1,3 and 1,6; 2-ethyl-hexanediol 1,3; pentanediol 1,3; 2-methyl-2-ethyl propanediol 1,3; 2-butyl-2-ethyl propanediol 1,3; hydroxy pivalyl hydroxy pivalate; decanediol 1,10; dodecanediol 1,12; and like materials. Up to about 10 mole % of the diol component may also be replaced with one or more triols, and thus the term "polyesterdiol" is inclusive of such polyester(poly)ols which would result. Diethylene glycol, triethylene glycol, dipropylene glycol, tripropylene glycol and the like can also be used according to the present invention to produce low viscosity polyesterdiols. However, incorporation of the ether group is detrimental to oxidation stability of the polyesters and products containing such polyesters.

In order to avoid the development of a polyesterdiol product which is crystalline at room temperature, it is preferred to avoid the combination of the single linear aliphatic dicarboxylic acid component adipic acid and the single linear diol component ethylene glycol. Where linear acids or diols are used exclusively, crystallization may be avoided by using a combination of at least two different linear acids and/or a combination of at least two different linear diols. Most preferably, the diol component consists of a 1,2 or 1,3 branched chain diol having at least one alkyl substituent group at the alpha or beta positions from a hydroxyl group, because aliphatic polyesterdiols containing these branched chain diol components offer the best resistance to transesterification and hydrolysis of the polyesterdiol.

One of the key factors towards achieving polyester diols having both low molecular weight and narrow molecular weight distribution is that the esterification reaction is conducted using a molar excess of diol. The molar ratio of diol to diacid should be greater than 1.5 to 1 up to about 6 to 1, more preferably from about 2:1 up to about 4:1. These diols to diacid ratios form strong synergy with high stability to transesterification.

The combination of higher diol to diacid ratio combined with removal of unreacted diol without significant transesterification impart a lower molecular weight and more narrow molecular weight distribution to the polyesterdiols and both of these factors are beneficial for the development of lower viscosity of the polyester diols. As a result, polyesterdiols with a polydispersity (polydispersion coefficient) Mw/Mn of less than 1.4, preferably less than 1.35, more preferably less than 1.3 and most preferably less than 1.25 are readily produced. A special absolute calibration GPC Technique was developed to determine molecular weights, molecular weight distribution and polydispersion coefficients for the polyesterdiols produced according to present invention, as described below.

The esterification reaction may be conducted in the presence or absence of a conventional esterification catalyst. The addition of proper catalysts can be beneficial in accelerating the reaction, and catalysts are required where the dicarboxylic acid is in the form of the dialkyl ester derivative. Suitable catalysts for the reaction include numerous oxides, salts, and alcoholates of Group II to V metals, such as Zn, Sn, Al, Mn, and Ti which are known as esterification and transesterification catalysts. Other catalysts include such metalloid compounds as $B_2O_3$, $H_3BO_3$, $Sb_2O_3$, $As_2O_3$, etc. The catalyst employed can also be a weak acid such as phosphorous acid, phosphoric acid, or hypophosphorous acid, or a strong acid catalyst such as p-toluene sulfonic acid and methane sulfonic acid. Preferred catalysts include titanium tetra butylate or isopropylate. The catalyst is generally employed at catalytic levels based on the weight of the reactants, typically from about 0.01 to about 2.0 wt %, more preferably from about 0.05 to 1.5 wt %.

Where a catalyst is employed in the esterification reaction, it must be substantially removed from the polyesterdiol reaction product prior to stripping excess diol from the product. Sufficient catalyst should be removed such that the resulting product contains less than catalytic quantities of residual catalyst. If the catalyst is not removed, it will tend to catalyze transesterification (ester exchange) reactions during the stripping process, leading to products having unacceptable properties in terms of molecular weight, molecular weight distribution, viscosity, NVM and catalytic impurity content.

The catalyst is preferably removed by treating the polyesterdiol reaction product containing residual catalyst with an agent which will convert the catalyst to a form which is insoluble in the reaction product, followed by removing, e.g., filtering, the treated reaction product to remove precipitated insoluble catalyst particles. One preferred method for catalyst removal is hydrolysis of hydrolyzable catalyst by adding water or mildly alkaline water to the reaction product and heating the product at about 75°–100° C. for a period of time sufficient to hydrolyze the catalyst and form the insoluble catalyst hydrolysis product. Another technique involves in-situ conversion of the catalyst to a reaction product-insoluble salt, followed by removal, e.g., filtration, of the insolubilized particles as described above. Other techniques for catalyst insolubilization will occur to those skilled in the art. While the catalyst may not be totally precipitated out by such processes, sufficient catalyst should be removed such that any residual catalyst in the polyesterdiol reaction product is present at less than catalytic quantities, preferably below about 0.01 wt %, based on the weight of polyesterdiol reaction product.

The polyesterdiols may be prepared by conventional esterification reactions wherein a mixture of dicarboxylic acid or acid derivative and diol, along with catalyst where present, and optional organic solvent, e.g., toluene, are heated under inert atmosphere in a stirred reactor equipped with condenser. Esterification is conducted by gradually raising the temperature of the reaction mixture from about 140° C. up to about 270° C. where no catalyst is used, more preferably from about 140° C. to about 240° C. Where esterification catalyst is used, the maximum heating temperature preferably lies in the range of 200°–240° C. However, in many cases the required acid number can be achieved at temperatures below the above recited maximums.

Heating is continued until the evolution of water or $C_1$ to $C_4$ alcohol is essentially complete and a polyesterdiol having an acid number of less than 20, preferably less than 10, more preferably less than 5 and most preferably less than 3 is achieved. Addition during the reaction of small amounts of an epoxy compound will form ester groups with free carboxylic acid groups, thereby assisting in achieving the these low acid numbers. Suitable epoxy compounds include ethylene oxide, propylene oxide, butylene oxide and glycidyl esters of carboxylic acids, particularly glycidyl esters of neoacids. An example of the latter is the glycidyl ester of neodecanoic acid marketed by Exxon Chemical Co. under the trade name Glydexxe® N-10.

Removal of unreacted diol from the polyesterdiol reaction product may be conducted using conventional distillation techniques. Typically the distillation is conducted at reduced pressure, e.g., about 300 to 0.01 torr, and at temperatures above 100° C. up to generally below the atmospheric boiling point of the reaction mixture, preferably below about 220° C., more preferably below about 200° C., and most preferably below about 180° C. Because the polyesterdiols of the present invention are resistant to transesterification and hydrolysis, water in the form of steam can be added to the polyesterdiol reaction product during distillation to facilitate removal of excess diol. Generally distillation is conducted until at least about 75 wt %, more preferably at least about 90 wt % of unreacted diol present in the polyester diol is removed such that the resultant polyester diol has an NVM content of greater than about 96 wt %, preferably greater than 98 wt %, more preferably greater than 99 wt %, up to about 100 wt %.

As indicated above, the polyesterdiols of this invention are characterized as having low viscosities of less than 3500 cps, preferably less than 3000 cps and more preferably in the range of from about 300 to 2,000 cps, even more preferably in the range of from about 300 to less than 1,000 cps. For the purposes of this invention, polyesterdiol viscosities are determined using a Brookfield viscometer at 25° C.

The number average molecular weight of the polyesterdiols of the invention is generally up to about 1,000, more preferably in the range of about 250 to 600. Molecular weight (number and weight average) is determined by GPC (Gel Permeation Chromatography), as described below.

Conventional methods for determining molecular weight (MW) and molecular weight distribution (MWD) by GPC., such as disclosed in U.S. Pat. No. 4,540,771, are not actual measures of "real" MW or MWD. To better define these real values, a self calibrating GPC technique was developed.

The GPC system that has been used for the analysis of polyester samples is a standard Waters System. Instrument descriptions are as follows:

Waters 590 HPLC Pump

Waters 410 Differential Refractometer

Waters 717 Auto sampler

Waters Millennium V2.10 software

Jordi 1000 Angstrom GPC Column

Dell 486 Computer

The analysis is run using tetrahydrofuran (THF) at a carrier rate of 0.8 mls min. Samples are prepared at a concentration of 1 to 5% in THF and 25 ml. of the diluted sample in THF is injected into the column. Column and refractometer temperatures are maintained at 35° C. Analysis time is typically 20 min.

The NPG/adipate used was found by inspection to be a homologous series of compounds, with increments of NPG-Adipate molecular units, as indicated in FIG. 1. Although it is seemingly obvious that the compounds are sequential members of the NPG Adipate-NPG (Adipate-NPG) . . . series; the sample identification was verified to 1500 MW using GC-Mass Spectrometry. This exact molecular weight information can then be used to calibrate the GPC for this adipate.

A similar technique can be used to calibrate the GPC for polyesters containing a limited number of monomers. For 2 monomers (1 diacid and 1 diol) where the diol is in excess, and where the reaction is driven close to 100%, polyesters consisting of individual fractions with exactly known molecular weights are formed. $M_1$=2Mw Diol+1Mw Diacid−36.0. Each heavier fraction has one more diacid and one more diol and add an increment of molecular weight as follows:

1 Mw diol+1 Mw diacid−36.0=ΔM Mi+1=Mi+ΔM

For NPG Adipate, $M_1$=318.4 and ΔM=214.3 which gives $M_2$=532.7, $M_3$=747, $M_4$=961.3, etc. A similar set of fraction molecular weights can be calculated for other polyesterdiols. For example, propylene glycol adipate (PGAd) would have: $M_1$=262.3 ΔM=186.2 which would give $M_2$=448.5, $M_3$=634.7, $M_4$=820.9 etc.

These simple calculations can be extended to more complex systems. For example, if one reacts a mixture of adipic and glutaric acids in a 1 to 1 molar ratio, one can use $$\frac{MwAd + MwGlut}{2}$$

as the molecular weight of the diacid to calculate both $M_1$ and ΔM. In this case $M_{wAcid}$=139.13 and for ethylene glycol adipate-glutarate we have: $M_1$=227.2 and ΔM=165.2 and $M_2$=392.4, $M_3$=557.6, $M_4$=722.8, etc. The same approach can be used for mixtures of glycols. When the molecular weight of fractions for different polyesterdiols were assigned to actual peaks on the GPC, an absolute calibration can be made as straight line retention time for a peak versus In $M_i$ for the polyester diol. Taking the first 3–4 most distinct peaks, a regression coefficient of 0.998–0.999 was demonstrated for all polyesterdiols evaluated. In analyzing the GPC chromatogram, one should understand that real fractions are individual compounds and actual chromatograms providing zones instead of just a line corresponding to the individual compound are artifacts inherent to the GPC method. This phenomenon is called "zone broadening". FIG. 1 presents data for NPG Adipate of Example 1 demonstrating the phenomena and the basis of the technique.

For any fraction, one can define the area between molecular weights Mi±½ ΔM as the area of the fraction with the molecular weight Mi. This assignment of areas produce set of data:

$M_1$—Area 1 between $M_1$−½ΔM and $M_1$+½ΔM.
$M_2$—Area 2 between $M_1$+½ΔM and $M_2$+½ΔM.
$M_3$—Area 3 between $M_2$+½ΔM and $M_3$+½ΔM.
$M_i$—Area i between $M_{i-1}$+½ΔM and $M_i$+½ΔM . . . etc.
Calculation should stop at $$\text{Area} < 0.1\% \text{ of } \sum_{i=1}^{n} \text{Area } i:$$

Then the molecular weights are calculated by the formulas:

$$Mn = \frac{\sum_{i=1}^{n} \text{Area } i}{\sum_{i=1}^{n} \frac{\text{Area } i}{M_i}} \quad Mw = \frac{\sum_{i=1}^{n} \text{Area } i \cdot M_i}{\sum_{i=1}^{n} \text{Area } i}$$

Polydispersion coefficient is $\frac{M_w}{M_n}$

The polydispersion coefficient is by definition equal to 1 for individual compounds. The smaller the polydispersion coefficient, the more narrow is the molecular weight distribution.

The polyesterdiols of the present invention may be used as a curable resinous component in thermosettable paint, adhesive and coating compositions in combination with amino or polyisocyanate crosslinking agents. They may also be used in such systems in combination with a phenol functional hardening agent which is also reactive with the crosslinking agents, e.g., bis-phenolic compounds such as bisphenol-A, aromatic polyhydric phenols of the type disclosed in U.S. Pat. No. 5,166,289, the disclosure of which is incorporated herein by reference, and polyester oligomers containing a reactive hydroxyl group and a terminal phenolic group of the type disclosed in copending U.S. applications Ser. No. 08/480,076, filed in the U.S. Patent Office on Jun. 7, 1995 and Ser. No. 08/424,205, filed in the U.S. Patent Office on Apr. 19, 1995. Such hardening agents may be present in the composition at a level of about 1 to 50 wt %, more preferably from about 2 to 30 wt %, based on the weight of curable polymer, polyesterdiol and crosslinking agent present in the composition.

The polyesterdiols of this invention are also suitable for use as a reactive diluent in curable compositions containing one or more di-or polyhydroxy functional polymer components such as acrylic polymers, polyesters, alkyd resins, epoxy resins, polyether polymers, polycarbonate polymers, mixtures thereof and like materials. A particularly advantageous use is as a reactive diluent in combination with phenol terminated, non-liquid crystalline diester polymers of the type disclosed in U.S. Pat. No. 5,210,155 and U.S. Pat. No. 5,239,018, the complete disclosures of which are incorporated herein by reference.

Preferred di-or polyhydroxy functional polymer components include one or a mixture of a poly(oligo)meric polymer components selected from the group consisting of di-(poly)esters, alkyd resins, acrylic resins, polyether polymers, polycarbonate resins, and poly(oligo)mers which contain a combination of two or more of ester, ether, carbonate, acrylic and alkyd moieties in their structure, said polymeric component further characterized as having a number average molecular weight within the range of about 250 to about 20,000. The polyesterdiol is normally present in such compositions at of weight level of from about 1–50 wt %, more preferably from about 5 to 45 wt %, based on the combined weight of di-or polyhydroxy functional polymer and crosslinking agent present in the composition.

Use of the polyester diols in combination with other curable resin systems facilitates the development of low viscosity, high solids content coating formulations having a very low VOC content. Because of the very low viscosity and narrow molecular weight distribution of the polyesterdiols, they effectively serve as a reactive diluent in such formulations thereby either eliminating the need to use auxiliary solvents to achieve workable coating formulation viscosities, or at least reducing the amount of such auxiliary solvents which need to be added to such coating formulations in order to achieve workable viscosities.

Suitable amino crosslinking agents which may be used in compositions containing the polyesterdiols of the present invention are those materials which will chemically react with the hydroxyl terminal groups of the polyester. Suitable materials include, butylated or methylated urea-formaldehyde resins, butylated melamine-formaldehyde resins, hexaalkoxymethylmelamines containing $C_1$ to $C_4$ alkoxy groups such as hexamethoxymethyl melamine or hexabutoxymethyl melamine, or mixtures of various hydroxymethoxymethylmelamimes, tetramethoxymethyl glycoluryl, polymeric melamines, etc. The hydroxymethylmelamine and hydroxymethyl ureas may also be etherified with alcohols other than methyl or butyl such as ethyl, propyl, isobutyl and isopropyl. Suitable amino crosslinking agents are described in the aforementioned U.S. Pat. No. 5,166,289. The content of amino crosslinking agent should be such that the ratio of the active crosslinking groups, e.g., methylol (alkoxylmethyl) groups of the crosslinking agent to hydroxyl groups present in the polyesterdiol and other reactive components is desirably from about 1:1 to about 7:1, more preferably from about 1.5:1 to 4.5:1 and most preferably from about 2:1 to 3:1.

When used in combination with a hardening component, such as described in U.S. Pat. No. 4,104,240, U.S. Pat. No. 4,540,771, and especially as described in U.S. Pat. No. 5,166,289, U.S. patent application Ser. No. 08/480,076 and Ser. No. 08/424,205, the hardening agents should be used in mixture with appropriate level of aminocrosslinking agent. Particular types and quantities of aminocrosslinking agents can be found in the above U.S. Patents and patent applications, the complete disclosures of which are incorporated herein by reference.

Suitable polyisocyanates which may be used as crosslinking agents include monomeric polyisocyanates such as toluelene diisocyanate and 4,4'-methylene-bis-(cyclohexyl isocyanate), isophorone diisocyanate and NCO-prepolymers such as the reaction products of monomeric polyisocyanate such as those mentioned above with polyester or polyether polyols, including the polyesterdiols disclosed in this invention. Other useful isocyanates are the isocyanurates from isophorone isocyanate commercially available from Huls Company as T1890 1,6-Hexamethylene diisocyanate and the biuret from 1,6-hexamethylene diisocyanate commercially available from Mobay Chemical Company as DESMODUR N. The polyisocyanate can be blocked with suitable blocking agents which would unblock at elevated temperatures such as a low aliphatic alcohols, e.g., methanol, oximes such as methylethyl ketone oxime and lactams such as caprolactam. The fact that the polyesterdiols of the invention are of very high purity minimizes chemical interference with polyisocyanate curing agents.

Generally, the weight level of crosslinking agent present in the curable composition will range from about 3 to 60 wt %, more preferably from about 10 to 50 wt %, based on the combined weight of the binder, i.e., the weight crosslinkable constituents and crosslinking agent.

Coating formulations of the invention also preferably contain an acid catalyst to catalyze the crosslinking reaction. Such catalysts include, for example, p-toluene sulfonic acid, methane sulfonic acid, nonylbenzene sulfonic acid, dinonyl naphthalene monosulfonic acid, dinonylnapthalene disulfonic acid, dodecylbenzene sulfonic acid, phosphoric acid, phosphorous acid, phenyl acid phosphate, butyl phosphate, butyl maleate, and the like or a compatible mixture of them. These acid catalysts may be used in their neat, unblocked form or combined with suitable blocking agents such as amines. Typical examples of unblocked catalysts are the King Industries, Inc. products with the tradename K-CURE®. Examples of blocked catalysts are the King Industries, Inc. products with the tradename NACURE®. The content of catalyst may generally range from about 0.02 up to about 2 wt %, preferably from about 0.1 to about 0.4 wt %, based on the weight of binder present in the composition. Binder refers to the combined weight of polyester diol and other curable components plus the weight of crosslinking agent.

Because of the very low viscosity of the polyesterdiols of the present invention, they can be used in curable coating formulations, alone or in combination with hardening agents, without the need to use a large amount of, if any, additional solvents to achieve workable viscosities and provide an excellent binder for high solids and ultra high solids compositions providing an excellent balance of cured coating properties and low VOC. Suitable optional solvents which may be included in the curable compositions of the invention comprise toluene, xylene, ethylbenzene, tetralin, naphthalene, and solvents which are narrow cut aromatic solvents comprising $C_8$ to $C_{13}$ aromatics such as those marketed by Exxon Chemical Company under the name Aromatic 100, Aromatic 150, and Aromatic 200.

Other suitable solvents include acetone, methyl ethyl ketone, methyl isobutyl ketone, methyl amyl ketone, methyl isoamyl ketone, methyl heptyl ketone, isophorone, isopropanol, n-butanol, sec.-butanol, isobutanol, amyl alcohol, isoamyl alcohol, hexanols, and heptanols.

Suitable oxygenated solvents include propylene glycol monomethyl ether acetate, propylene glycol propyl ether acetate, ethyl ethoxypropionate, dipropylene glycol monomethyl ether acetate, propylene glycol monomethyl ether, and like materials. Other such solvents include alkyl esters such as ethyl acetate, n-propyl acetate, butyl acetate, amyl acetate, mixtures of hexyl acetates such as sold by Exxon Chemical Company under the name EXXATE® 600 and mixtures of heptyl acetates sold under the name EXXATE® 700. The list should not be considered as limiting, but rather as examples of solvents which are useful in the present invention. The type and concentration of solvents are generally selected to obtain formulation viscosities and evaporation rates suitable for the application and baking of the coatings. Typical solvent concentrations in the formulations range from 0 to about 75% by weight. Where solvents are used, they are present at a preferred range between about 5 and 50% by weight and a most preferred range between about 10 and 40% by weight. For the preparation of high solids coatings, the amount of solvent used in the coating formulation is preferably less than 40% of the weight of the formulation, more preferably less than 20% by weight.

Pigments are a further component which may be present in the curable compositions of this invention. They are generally included at a weight ratio in the range of from about 0.1 to about 5.0 to one pigment-to-binder ratio, the term binder referring to the total weight of curable components plus crosslinking agent.

Suitable pigments which may be included in the compositions of this invention are organic and inorganic pigments normally used in paint and coating formulations and include titanium dioxide, zirconium oxide, zircon, zinc oxide, iron oxides, antimony oxide, carbon black, as well as chrome yellows, greens, oranges, mixed metal oxides, ceramic pigments and the like. Preferred pigments include rutile $TiO_2$ and particularly weather resistant coated types of $TiO_2$. The pigments may also be blended with a suitable extender material which does not contribute significantly to hiding power. Suitable extenders include silica, barytes, calcium sulfate, magnesium silicate (talc), aluminum oxide, aluminum hydroxide, aluminum silicate, calcium silicate, calcium carbonate, potassium aluminum silicate and other clays or clay-like materials.

Organic Pigments such as Phthalocyanines, Anthraquinones, Quinacridones, Pyranthrones, etc., and their combinations with inorganic pigments are also suitable for compositions of this invention.

The composition of this invention may also contain other additives which are conventionally used in paint and coating compositions such as flow control (anti sag) agents, e.g., silicones, fluorocarbons or cellulosics; flatting agents; wetting agents; UV stabilizers; anti-foaming agents; fungicides and the like.

Satisfactory baking schedules for formulations of the present invention vary widely including, but not limited to, low temperature bakes of about 20 to 30 minutes at temperatures between 90 and 105° C. for large equipment applications and high temperature bakes of about 5 to 60 seconds in 300 to 375° C. air for coil coating applications.

In general, the substrate and coating should be baked at a sufficiently high temperature for a sufficiently long time so that essentially all solvents are evaporated from the film and chemical reactions between the polymer and the crosslinking agent proceed to the desired degree of completion. The desired degree of completion also varies widely and depends on the particular combination of cured film properties required for a given application.

The following examples are illustrative of a first embodiment of the invention.

EXAMPLE 1

This example shows the preparation of a polyesterdiol of adipic acid and neopentyl glycol under catalyst free conditions.

Into a 5 liter round bottom, 4 neck reaction flask equipped with a heating mantel, stirrer, thermometer, condenser and Dean Stark Trap was charged 2080 grams of neopentyl glycol (NPG) and 1460 grams of adipic acid (about a 2:1 molar ratio of diol to diacid). The reactor was purged with nitrogen and the contents were heated. At 130° C. all components were melted and upon further heating water began to distill. After 3.5 hours at 170° C., 365 grams of water phase, with a small amount of NPG, was distilled. The temperature was increased to 190° C., then to 210° C. and eventually to 230° C. An additional 63 grams of water phase was distilled. The polyesterdiol at this stage had an acid number (AN) of 6.3(mg KOH/gram product).

The polyesterdiol was then subjected to distillation conditions to remove excess unreacted NPG. The product was heated at 230° C. and the water phase formed during the synthesis was added to accelerate the NPG distillation. Distillation was continued for 8.5 hours at 230° C. during which time an additional 99 grams of water was charged into the reactor. After 8.5 hours, the condensate from the reactor was measured as about 979 grams, which included 459 grams of water and 520 grams NPG. The amount of NPG corresponds exactly to theoretical amount of unreacted NPG generated in the reaction without transesterification reactions taking place. The NPG adipate formed had an AN of 5.3, less than the original AN prior to distillation, which demonstrates the outstanding resistance to hydrolysis. The product had NVM content of 96% and viscosity of 2380 cps. The polyester was used in the first self calibration shown in FIG. 1.

These results may be compared with Example 8 of U.S. Pat. No. 4,922,002 wherein a similar NPG polyesterdiol was prepared in the presence of an esterification catalyst. The relatively high viscosity (3700 cps) is indicative that the product undergoes severe transesterification during distillation resulting in increased molecular weight and a broadening of molecular weight distribution.

EXAMPLE 2

This example demonstrates the preparation of NPG adipate under catalyst free conditions at a molar ratio of diol to diacid of about 3:1.

Into a 5 liter, 4 neck round bottom flask equipped with a heating mantle, a thermocouple fitted with a temperature controller, a mechanical stirrer, nitrogen port, a liquids addition funnel and a 10 inch packed column on the top of which is a Dean Stark Trap attached to a chilled water condenser, were charged 1872.8 grams neopentyl glycol (NPG) and 876.8 grams adipic acid (AA). The reactor was heated and stirring under the nitrogen sweep was initiated when the reactor contents were melted, at about 120° C. Gradual addition of toluene (non-reacting solvent) through the liquids addition funnel started at 144° C. and it was regulated such that vapor reflux was maintained throughout the synthesis. The solvent and water started distilling out overhead where they were condensed, collected and phase separated in the Dean Stark Trap. The solvent was continuously refluxed back to the reactor through the packed column while the water was drained and measured in order to monitor the reaction progress. Heating continued to a final temperature of 235° C. The reaction was stopped after 208 grams water (216 grams theoretical) were removed. The product had:

NVM (non-volatile matter)=68.9%

AN (acid number)=3.97

The following example illustrates the preparation of a polyesterdiol using mixed dimethyl esters as a reactant and the use of an esterification catalyst.

EXAMPLE 3

Transesterification of Mixed Dibasic Esters (Dimethyl Adipate, Glutarate and Succinate) with NPG.

The same apparatus as in Example 2 was used except for a two liter flask and magnetic instead of mechanical stirring and a vacuum line was connected at the condenser vapor outlet. The charge was 624 grams NPG and 318 grams dibasic esters (commercial blend of 0.5:1.6:0.6 mole ratio of dimethyl adipate:dimethyl glutarate: dimethyl succinate produced by DuPont). The reaction was heated to 98° C. to melt the contents. At this temperature 2.36 grams of titanium (IV) butoxide catalyst was added to the reactor and nitrogen sparge started. At 168° C. vacuum was pulled gradually to reduce the reactor pressure from 760 mmHg (atmospheric) to a final 660 mmHg. The reactor contents were heated to a final temperature of 180° C. The reaction was stopped when 114.9 grams methanol by-product (128 grams theoretical) was collected overhead.

The following examples 4 and 5 illustrate methods for stripping excess diol from polyesterdiols.

EXAMPLE 4

Steam Stripping of Excess NPG at 160° C.

Part of the polyester diol of Example 2 was placed in a 3 liter round bottom flask equipped with a heating mantle, a thermocouple fitted with a temperature controller, a magnetic stirrer, a nitrogen line, a steam sparger and a chilled water condenser connected to a single neck spherical flask with vacuum line outlet. The reactor contents were heated under nitrogen sweep until a temperature of about 92° C. was reached. At this point, vacuum was pulled to reduce the reactor pressure from 760 mmHg (atmospheric) to 100 mmHg. Heating was continued until 160° C. was reached. Steam was introduced into the reactor by vigorous sparging near the bottom of the flask. The steam and the dissolved NPG overhead were cooled in the condenser and collected in the spherical flask. The procedure was stopped when the NPG content in the reactor was less than 1 wt % by GC.

The final product had:

AN=3.23

NVM=100%

Viscosity=1750 cps at 25° C.

EXAMPLE 5

Steam Stripping of Excess NPG at 200° C.

Another part of the polyester diol of Example 2 was processed as in Example 4 except the stripping temperature was 200° C. under 440 mmHg vacuum.

The final product had:

AN=2.76

NVM=100%

Viscosity=1850 centipoises at 25° C.

Examples 4 and 5 demonstrate the high stability of the polyesterdiols to steam distillation even at temperatures of 160° C. and 200° C. NPG was able to be distilled almost quantitatively (NVM=100%) and yet the viscosity of the resulting polyesterdiols was approximately 50% of the viscosity achieved in Example 8 of U.S. Pat. No. 4,922,022.

The following examples illustrate catalyst removal prior to stripping unreacted diol (Example 6) and the effect on viscosity when catalyst is not removed prior to stripping (Example 7).

EXAMPLE 6

Part of the polyester diol produced in Example 3 was placed in a 1 liter round bottom flask and 4.2 wt % water was added. The contents were heated to 90° C. for 1 hour at atmospheric pressure and stirring. After 1 hour at 90° C., the pressure was reduced to 100 mmHg vacuum. After 1 hour at these conditions, the product was filtered hot through a Buchner funnel with filter paper and filter aid (0. 5" layer of Dicalite) fitted on a vacuum flask which was connected to a vacuum line. Vacuum was pulled and the filter aid was packed (pressed down). The hot polyester diol material was poured slowly into the filter cake. The filtrate was transferred to a round bottom flask for steam stripping the excess NPG as described in Example 4 at 160° C. under 300 mmHg vacuum.

The final product had:

NVM=96.4%

Viscosity=1605 centipoises at 25° C.

Titanium Metal content=<10 ppm (undetectable)

EXAMPLE 7

Effect of Catalyst Presence on Viscosity.

For comparison with Example 6, another part of the polyester diol from Example 3 was steam stripped to remove the excess NPG by the procedure described in Example 4, but without hydrolyzing and removing the catalyst prior to stripping.

The final product had:

NVM=98.4%.

Viscosity=3763 centipoises at 25° C.

Titanium metal content=580 ppm.

Example 6 illustrates that removal or reduction of catalyst level to less than catalytic quantities prior to distillation provides a polyester diol of very low viscosity (about 1600 cps) whereas failure to remove the catalyst as in Example 7 results in a polyester diol of higher viscosity (about 3760 cps), similar to Example 8 of U.S. Pat. No. 4,922,002.

EXAMPLE 8–9

Two additional polyesterdiols were prepared by the general procedure of Example 2 and without using an esterification catalyst, but at different molar ratios of diol to adipic acid as shown in Table 1. The polyester diols were steam stripped by the process described in Example 4. Comparative data with respect to the properties of the products of Examples 4, 8 and 9 are shown in Table 1.

TABLE 1

|  | NPG/Acid Ratio | VISC. (cps) | NVM | AN |
|---|---|---|---|---|
| Ex. 9 | 2:1 | 2050 | 100 | — |
| Ex. 4 | 3:1 | 1750 | 100 | 3.2 |
| Ex. 8 | 4:1 | 1400 | 100 | 1.7 |

These NPG adipates exhibit the highest NVM content and lowest viscosities of any known NPG adipates either commercially available or referred to in the literature. The following Examples 10–12 illustrate various methods for stripping unreacted diol and properties of the resultant polyester diol produced from propylene glycol and adipic acid.

EXAMPLE 10

A polyester diol from propylene glycol 1, 2 and adipic acid was prepared without the use of an esterification catalyst by the general process of Example 2 using 1520 grams of diol and 1460 grams of adipic acid reactants (about a 2:1 respective molar ratio). The pre-stripped polyester diol had an AN of 1.8 and an NVM content of 87.5%.

EXAMPLE 11

The polyesterdiol produced in Example 10 was vacuum stripped of unreacted propylene glycol using the general procedure of Example 4, except that a 2 liter reactor flask was used with magnetic stirring and without steam. The polyester diol of Example 10 was heated to 150° C. and full vacuum was pulled while maintaining the reactor temperature at 150° C. The procedure was terminated when 333 grams of propylene glycol was stripped off. The final product had:

Viscosity=695 cps

NVM=99.3%

AN=1.52

EXAMPLE 12

Wiped Film Evaporation:

A Pope wiped-film still, 2" model with 0.35 sq. ft. evaporator surface was used to remove excess 1,2-propane diol from a polyester diol prepared as described in Example 10. The wiped-film still was equipped with a feed flask, an internal condenser, receiving flasks at the bottom of the evaporator body (residue and distillate flasks) and an external condenser connected to a vacuum line. The feed flask was charged with 460 grams of the polyester diol. The evaporator body was heated up to 150° C. with cooling in the internal condenser. At 150° C. the wiper blade drive was turned on and the flow of the polyester diol was started at the rate of 2.5 grams/min under 3 mmHg vacuum. 56.1 grams of 1,2-propane diol was collected in the distillate flask and 398.3 grams of the polyester diol was collected in the residue flask.

The resulting product had an NVM content of 100% and a Brookfield viscosity of 658 cps.

GPC analysis for the product of Examples 11 and 12 were determined using the above described absolute calibration method. Results were as follows:

|  | Number Ave. MW (Mn) | Weight Ave. MW (Mw) | Dispersity (Mw/Mn) |
|---|---|---|---|
| Ex. 11 | 459.1 | 609.4 | 1.327 |
| Ex. 12 | 461.2 | 612.2 | 1.328 |

EXAMPLES 13–14

The following examples 13 and 14 demonstrate the stability of the polyester diols of this invention against transesterification during stripping of excess diol as reflected by GPC data. The polyesterdiol used in these examples was similar to that used in Example 10 except that 1826 grams of propylene glycol and 1169 grams of adipic acid were reacted, a 3:1 diol/diacid ratio. The reaction of Example 13 was stopped at an acid number of 12.3; the reaction of Example 14 was continued until an acid number of 2.2 was obtained.

The polyester diols prepared above were then each stripped according to the stripping processes of Example 11. GPC and other data is shown in Table 2.

TABLE 2

|  | Mn | Mw | (Mw/Mn) | NVM | VISC (cps) |
|---|---|---|---|---|---|
| Ex. 13 Pre Strip | 356.5 | 427.7 | 1.20 | — | — |
| Post Strip (Ex. 11) | 351.1 | 418 | 1.19 | 100 | 465 |
| Post Strip (Ex. 12) | 350.6 | 417 | 1.19 | 98.9 | 402 |
| Ex. 14 Pre Strip | 357 | 428.4 | 1.20 | — | — |
| Post Strip (Ex. 11) | 349.6 | 416 | 1.19 | 100 | 467 |
| Post Strip (Ex. 12) | 344.4 | 407 | 1.18 | 99.2 | 457 |

The data in Table 2 and FIGS. 2 and 3 demonstrate that the polyester diols prepared according to this invention have essentially identical molecular weights and molecular weight distribution before and after stripping unreacted diol and therefore demonstrate outstanding stability to transesterification at acid numbers of about 12 and 2, as well as the achievement of a combination of very low viscosities and high NVM content.

EXAMPLES 15–27

Tables 3 and 4 list a number of different polyester diols prepared in accordance with the general process of Example 10 and stripped in accordance with the general process of Example 11, and provides composition and GPC data for the resulting products. Diol ratios of 2:1 are used in Table 3 and diol ratio of 3:1 are used in Table 4.

TABLE 3

| | Mol. Ratio | | | | GPC | | |
|---|---|---|---|---|---|---|---|
| Ex. | Diol* | Diacid* | Diol/Diac | NVM | Visc (cps) | Mn | Mw | Disp. |
| 15 | 1,3B | GL. | 2 | 100 | 492 | 433 | 545 | 1.27 |
| 16 | 1,3B | AD. | 2 | 100 | 464 | 483 | 629 | 1.30 |
| 17 | 1,3B | SU. | 2 | 99.3 | 1115 | 411.5 | 520 | 1.26 |
| 18 | 2-MP | AD. | 2 | 100 | 700 | — | — | — |
| 19 | PG1,2 | SEB. | 2 | 100 | 560 | 580 | 798 | 1.38 |
| 20 | 1,2B | AD. | 2 | 100 | 593 | 476 | 618 | 1.30 |
| 21 | 1,2B | SU. | 2 | 99.1 | 1685 | 415 | 526 | 1.27 |

TABLE 4

| | Mol. Ratio | | | | GPC | | |
|---|---|---|---|---|---|---|---|
| Ex. | Diol* | Diacid* | Diol/Diac | NVM | (cps) | Mn | Mw | Disp. |
| 22 | PG1,2 | SEB. | 3 | 100 | 437 | 490 | 626 | 1.27 |
| 23 | PG1,2 | SU. | 3 | 99 | 1500 | 312 | 368 | 1.18 |
| 24 | 1,3B | AD. | 3 | 99.9 | 333 | 385 | 455 | 1.18 |
| 25 | 1,2B | AD. | 3 | 100 | 429 | 403 | 484 | 1.20 |
| 26 | PG1,3 | SU. | 3 | 100 | 448 | 325 | 390 | 1.20 |
| 27 | 1,3B | SU. | 3 | 99.7 | 666 | 347 | 405 | 1.17 |

*1,2B — 1,2 butanediol
1,3B — 1,3 butanediol
2-MP — 2 methyl propane, 1,3
PG-1,2 — 1,2 propanediol
PG-1,3 — 1,3 propanediol
GL — glutaric acid
AD — adipic acid
SU — succinic acid
SEB — sebacic acid As can be seen from Table 3 (Examples 15–21), all the reactant combinations show the preparation of high NVM, narrow molecular weight distribution (Mw/Mn<1.4) polyesterdiols, even at a ratio of diol to diacid of 2. However, at this ratio, polydispersity (Mw/Mn of 1.26 to 1.38) is larger than at a higher ratio of diol to diacid (Mw/Mn of 1.17 to 1.27). Nevertheless, even at this ratio and depending on monomer selection, low to very low viscosity can be achieved. Among the diols, used in Examples 15–21, butanediol 1,3 provided the lowest viscosity, 2-methyl 1,3 propanediol provided viscosity about the same as 1,2-propanediol and significantly lower than NPG at the same monomer ratio.

It is peculiar that in Examples 17 and 21, succinic acid provided the lowest molecular weight polyesterdiols, low polydispersity, and yields polyesterdiols of relatively higher viscosity than other diacids at similar diol to diacid ratios.

Apparently higher concentrations of polar ester groups can contribute to the viscosity. On the other hand, it appears that sebacic acid provides the lowest viscosity at the same diol to diacid ratio, despite the highest molecular weight pertinent to sebacic acid polyesterdiols.

The data of Table 4 (Examples 22–27) demonstrates that generally at a 3 to 1 diol to diacid ratio, significantly lower viscosity and more narrow molecular weight distributions for stripped products can be achieved. An especially low viscosity (333 cps) was achieved for butanediol 1,3-adipate (Example 24). Butanediol 1,2 (Example 25) generates polyesterdiols of slightly higher viscosity. The advantage of Butanediol 1,3 versus PG-1,2 can be seen with succinic acid also (Examples 23 and 27).

Also, it can be seen from a comparison of Examples 23 and 26 that linear diols (PG-1,3) provide lower viscosity than branched diols (PG-1,2). The interesting feature of Example 26 is that the polyesterdiol is liquid, not crystalline as it is known for most of the binary polyesterdiols based on linear diacid and linear diols. Example 26 also demonstrates that totally linear polyesterdiols, if they are driven to a low AN (AN for Example 26=1.0), provide high stability to transesterification and hydrolysis.

It is obvious from the data that the present invention is applicable to totally linear polyesterdiols, independent of their crystallinity at room temperature.

The present invention is focused mainly on polyesterdiols which are liquid at ambient conditions. Crystalline polyesterdiols with very low viscosity in melted form and of high NVM, low molecular weight and narrow molecular weight distribution are included in the present invention and can be produced according to the present invention. Also, mixtures of 2 or more different crystalline polyesterdiols can form liquid polyesterdiol with very low viscosity and high NVM. The same can be applied to a mixture crystalline and liquid polyesterdiols which can produce very low viscosity and high NVM content.

EXAMPLES 28–32

The following examples demonstrate that low viscosity, low molecular weight and high NVM polyesterdiols can be prepared from mixtures of aliphatic linear diols or mixtures of aliphatic linear diacids. Polyester diols were prepared in accordance with the general process of Example 10 and stripped in accordance with the general process of Example 11. Table 5 sets forth the composition of these polyesterdiols and physical property data.

TABLE 5

| Ex. | Diols* | Diacids | Mol. Ratio Diol/Diacid | NVM | VISC (cps) |
|---|---|---|---|---|---|
| 28 | 1,4B/PG1,2 | AD | 1.5:1.5:1 | 99.4 | 382 |
| 29 | 1,4B/1,3B | AD | 1.5:1.5:1 | 100 | 329 |
| 30 | EG | AD/GL | 2:0.5:0.5 | 100 | 380 |
| 31 | 1,4B/2-MP | AD | 1:1:1 | 100 | 544 |
| 32 | 1,4B/1,3B | AD | 0.67:1.33:1 | 100 | 470 |

*EG - ethylene glycol
1,4-B - butanediol 1,4.

Examples 28–32 demonstrate additionally the use of linear diols in the preparation of low viscosity high NVM polyesterdiols according to the present invention. Example 30 demonstrates that another totally linear polyesterdiol based on linear diacids and ethylene glycol, which is a diol most sensitive to transesterification reactions, can be prepared according to the invention and provide extremely low viscosity (lowest viscosity for polyesterdiols prepared at diol to diacid ratio of 2) and high NVM. This demonstrates that if the reaction is driven to a low enough acid number (AN-0.68 for Example 30), the polyesterdiol exhibits outstanding stability to transesterification even if the structure consists of only linear diol and diacid moieties.

The above examples demonstrate the scope of the invention with respect to polyesterdiols which are the most difficult to produce without transesterification taking place. The present invention is also applicable to the preparation of polyesterdiols comprising ester groups derived from aliphatic diacid moieties and also containing moieties derived from cycloaliphatic and/or aromatic diacids. Incorporation of moieties derived from cycloaliphatic/aromatic diacids increase the viscosity of polyesterdiols, but can offer some advantages in other properties such as hardness.

Taking into consideration viscosity requirements, it is preferable to use less than 50% (molar) cycloaliphatic/aromatic diacids based on the sum of diacids, more preferably less than 20% and most preferably less than 10% cycloaliphatic/aromatic diacids.

Low molecular weight, narrow molecular weight distribution polyesterdiols of the present invention may be used in a wide variety of coating and adhesive compositions. The composition can optionally include other poly(oligo)mers, pigments, crosslinking agents, fillers, additives and solvents to satisfy requirements of the final product. Use of the polyesterdiols reduce the amount of solvent necessary to provide the properties required for the final composition and, therefore, reduce the VOC of the composition. The structure and composition of the polyesterdiols of the present invention provide significant advantages in different compositions generally unexpected for such compounds.

Because the polyesterdiols made in accordance with the present invention have relatively low glass transition temperatures (Tg), it would be expected that crosslinked coatings containing these materials would exhibit relatively low hardness values. This is unexpectedly not the case as shown hereafter.

Coating formulations of the present invention may be prepared by first forming a mill base. The mill base may be prepared by grinding a mixture of pigment, resin and solvent in a high speed disc disperser such as Byk-Gardner DISPERMAT® Model CV to form a pigment concentrate. This mill base is then let down (mixed) under mixing conditions with the remaining components of the formulation which include additional resin, solvent, crosslinking agent, and the catalyst.

The coating compositions of the invention may be applied to substrates by any suitable conventional technique such as spraying, roller coating, dip coating and the like. The composition may be applied in liquid form, and, if necessary, be dispersed in an organic solvent.

The following examples illustrate the preparation of various paint formulations, including formulations containing some of the polyesterdiols of the invention, used as either a reactive diluent or a substitute for some of the resinous binder components of the formulation. All components are present on a weight basis unless otherwise indicated.

The materials used in some of the following examples are identified as follows:

Joncryl™ 504—An acrylic polyester-polyol available from S. C. Johnson Co.

BYK™ P-104S—Dispersing additive produced by BYK-Chemie.

CYMEL™ 303—Hexa(methoxymethyl) melamine crosslinking resin—partially condensed (from American Cyanamid).

CYMEL™-300—Hexa(methoxymethyl) melamine crosslinking agent (from American Cyanamid).

Nacure™ 2500—Blocked p-toluene sulfonic acid catalyst from King Industries.

BYK™ 451—Blocked p-toluene sulfonic acid a catalyst from Byk-Chemie.

DC-57—Silicone flow control agent from Dow Corning (sometimes 10% in MIAK).

Solvent Mix—Mixture of 80 parts by wt. butanol-1,100 parts by wt. butyl acetate and 122 parts by wt. amyl acetate.

PED-55-225—polyesterdiol of neopentyl glycol and adipic acid having a viscosity of 3,000 cps and an NVM content of 93.3% by ASTM D-2369-90 marketed by Witco under the name Fomrez™ 55-225.

PED-33-225—polyesterdiol of propylene glycol and adipic acid having a viscosity of 1250 cps, NVM measured as about 96% by ASTM D-2369-90 and a polydispersity of 1.46, marketed by Witco under the name Fomrez™ 33-225.

Hardener A—an ester reaction product of para-hydroxybenzoica acid and a glycidyl ester of a mixed aliphatic, mostly tertiary monocarboxylic acids (neodecanoic acid) with an average of 9 to 11 carbon atoms, sometimes diluted to 83% with Aromatic 100 solvent, prepared as in Example 1 of U.S. patent application Ser. No. 424,205 filed Apr. 18, 1995. Molecular weight=366.

EXAMPLE 33 (Control)

A control paint formulation was prepared using a commercial acrylic polyesterpolyol as a polymeric binder component. A millbase was prepared by mixing and grinding the following compositions (in grams).

Millbase

Joncryl™ 504—400

Amyl Acetate—20

BYK™ P-104S—4

TiO$_2$ (R-960)—650.0 268.5 grams of the above millbase was further mixed (let down) with the following composition (in grams).

Joncry™ 504—85

CYMEL™ 303—63.5

Nacure™ 2500—2.5

DC-57—5

Solvent Mix—75.5

The resulting formulation had a Zahn #3 cup viscosity of 20 seconds and an NVM content of 73.33%; density of 11.15 and a VOC content of 2.90.

Test panels were prepared and evaluated as follows:

Thin films of the various formulations were applied to steel test panels via drawdowns. The basic procedures are outlined in ASTM Test Procedure D823-87. Test panels are polished Bonderite™ 1000 (iron-phosphate treatment) panels obtained from Advanced Coatings Technology Inc. Panels sizes are either 4"×8" or 3"×6".

Wire-wound drawdown rods and in some cases a Precision Laboratory Drawdown Machine (both from the Paul N. Gardner Company) are used to apply films via hand-pulled drawdowns (Method E). Target dry film thicknesses are 1 ml.

The film property evaluations conducted on all cured panels were as follows:

Knoop Hardness—ASTM D-1474

Direct Impact—ASTM D-2794

VOC—EPA Method 24

Pencil Hardness—ASTM D-3363

MEK RUBS—ASTM D-373

NVM—ASTM D-2369-90

Gloss—ASTM G-53

The formulation was applied by drawdown to a Bonderite™ steel panel and baked 20 minutes at 300° F. The cured baked coating had the following properties:

Gloss (20°)—80

Gloss (60°)—96

Pencil Hardness—4H

Knoop Hardness—16.0

Direct Impact—30

EXAMPLES 34–37

Formulations (in grams) as shown in Table 6 were prepared using the same millbase as in Example 33 but the Joncryl 504 acrylic polymer used in the let down of Example 34 was substituted with various polyesterdiols of the invention and two commercially available polyesterdiols as indicated in Table 6.

TABLE 6

| Example | 34 | 35 | 36 | 37 |
|---|---|---|---|---|
| Millbase Ex 33 | 107.4 | 107.4 | 107.4 | 107.4 |
| HMMM | 31.2 | 31.2 | 29.3 | 29.3 |
| Nacure ™ 2500 | 1.0 | 1.0 | 1.0 | 1.0 |
| Polyesterdiol (Ex 8) | 21.4 | — | — | — |
| Polyesterdiol (Ex 14) | — | 21.4 | — | — |
| PED-55-225 | — | — | 25.0 | — |
| PED-33-225 | — | — | — | 24.3 |
| Solvent Mix | 10 | 10 | 15 | 15 |

The polyesterdiol/HMMM weight ratio for Examples 34 and 35 was 55:45 and for Examples 36 and 37 was 60:40. The difference reflects difference in molecular weight and concentration of functional groups of the polyesterdiols of the present invention and commercial PED-55-225 and PED-33-225 products. The formulations were further adjusted with the solvent mix to the same viscosity as in Control Example 33, i.e., 20 minutes Zahn Cup #3.

The NVM and VOC contents for each equal viscosity formulation were as follows:

|  | Ex 34 | Ex 35 | Ex 36 | Ex 37 |
|---|---|---|---|---|
| NVM | 80.41 | 79.64 | 78.37 | 78.92 |
| VOC | 2.31 | 2.41 | 2.48 | 2.45 |

This data shows that compositions of the present invention (Ex. 34 and 35) having workable viscosities have higher NVM content and lower VOC content at equal viscosities with the compositions containing commercially available polyesterdiols (Ex. 36 and Ex. 37).

These formulations were then applied to Bonderite™ steel panels and baked 20 minutes at 300° F. as in Example 33. Properties of the cured baked panels are shown in Table 7.

TABLE 7

|  | Gloss | | Knoop | Pencil | MEK | Direct |
|---|---|---|---|---|---|---|
|  | 20° | 60° | Hardness | Hardness | RUBS | Impact |
| Ex 34 | 71 | 91 | 13.9 | 4H | >300 | 60 |
| Ex 35 | 73.5 | 93 | 13.7 | 4H | >300 | 60 |
| Ex 36 | 54 | 86 | 6.8 | F | >300 | 90 |
| Ex 37 | 61 | 77 | 5.0 | F | >300 | 90 |

As seen from Table 7, a substitution of up to 46% of the binder with reactive diluents based on polyesterdiols of the present invention provided outstanding properties to the coatings—very high hardness approaching the formulation of control Example 33 and better flexibility (resistance to Impact). Commercial products caused significant reduction in hardness as compared to the control. It should be understandable, that at lower level of reactive diluent based on commercial polyesterdiol, similar hardness can be achieved. By blending the Formulation of Example 33 with formulations of Examples 36 and 37 (prepared at the same viscosity) at different ratios, it can be demonstrated that it would require 19% substitution with reactive diluent based on Fomrez™ 55–225 and 15% substitution with reactive diluent based on Fomrez™ 33–225. Therefore, VOC reduction provided by the reactive diluents based on polyesterdiols of the present invention was about 0.5 to 0.6 lb/Gal., while the same properties with similar commercial polyesterdiols provides about 0.15 to 0.2 lb/Gal. reduction in VOC.

The polyesterdiols of the present invention may also be used in coating formulations in combination with other hardening components having a higher glass transition temperature (Tg), such as the aromatic polyesterdiols disclosed in U.S. Pat. Nos. 4,104,240 and 4,540,771, and particularly in combination with phenol-functional hardening components such as bisphenol A or those described in U.S. Pat. Nos. 5166289, 5210155 and 5239018 and U.S. patent applications Ser. Nos. 08/480,076 and 08/424,205. All of these patents are incorporated herein by reference.

One preferred class of hardening compounds include the bis aromatic polyhydric phenols as disclosed in U.S. Pat. No. 5,166,289 having the structure:

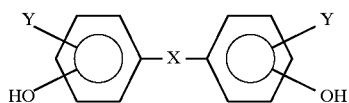

wherein X is selected from the group consisting of carbon to carbon covalent bond, oxygen, sulfur, —S—S—, —CO—, —SO—, —SO$_2$— and a divalent organic radical having a molecular weight less than about 400, and wherein Y is independently selected from the group consisting of hydrogen, halogen, $C_1$ to $C_4$ alkyl and $C_1$ to $C_4$ alkoxy.

Examples of preferred compounds are those of the formula wherein Y is hydrogen and include phenolphthalein, 2,2-bis(4-hydroxyphenyl)propane [bisphenol A], 1,1-bis(4-hydroxyphenyl)cyclohexane[bisphenol Z], 1,1-bis(4-hydroxyphenyl)ethane, bis(4-hydroxyphenyl)methane, 1,2-bis(4-hydroxyphenyl)ethane, bis(4-hydroxyphenyl) cyclohexylmethane, 3,3-bis(4-hydroxyphenyl)pentane, bis (4-hydroxyphenyl)ether, bis(4-hydroxyphenyl) sulfide, and 2,2-bis(4-hydroxyphenyl)hexafluoropropane.

Other such bis-aromatic polyhydric phenols include polyhydric phenol diesters which are the polycondensation product of a $C_2$ to $C_{20}$ aliphatic or cycloaliphatic diol such as neopentyl glycol with a 2:1 molar excess of para-hydroxybenzoic acid.

The hardening component disclosed in U.S. patent application Ser. No. 08/424,205 includes the ester reaction product of a para-hydroxy benzoic acid and an epoxy functional compound having the structure:

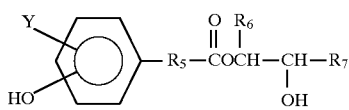

wherein $R_4$ and $R_6$ are preferably each hydrogen, $R_5$ is preferably a direct bond and $R_7$ is selected from the group consisting of $CH_2OH$, a hydrocarbon moiety containing 3 to about 20 carbon atoms and an organic moiety containing ester or ether groups and containing from 3 to about 20 carbon atoms. An example of such a hardener component is the ester reaction product of para-hydroxybenzoic acid and a glycidyl ester of Glydexx N-10 (mixed aliphatic, mostly tertiary monocarboxylic acids with an average of 9 to 11 carbon atoms), a product available from Exxon Chemical Company.

The chemical structure of this product, identified above as Hardener A, is as follows:

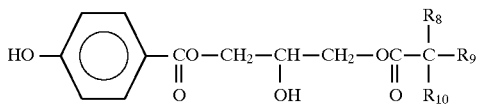

wherein $R_8$, $R_9$ and $R_{10}$ are the same or different $C_1$ to $C_4$ mixed alkyl groups totaling 3 to 12 carbon atoms, preferably about 8 carbon atoms.

EXAMPLES 38–42

Millbases having the following composition were prepared as disclosed above:

| Mill Base | A | B | C | D | E |
|---|---|---|---|---|---|
| Polyesterdiol Ex 8 | 66.7 | — | — | — | — |
| Polyesterdiol Ex 14 | — | 66.7 | — | — | — |
| PED-55-225 | — | — | 71.5 | — | — |
| PED-33-225 | — | — | — | 69.5 | — |
| Hardener A | — | — | — | — | 120.5 |
| BYK ™ P-104S | 0.82 | 0.82 | 0.82 | 0.82 | 1.23 |
| TiO$_2$ (R-960) | 133.3 | 133.3 | 133.3 | 133.3 | 200 |

Specific quantities of the above formulated millbases were further let down to provide paint formulations having formulas as set forth in Table 8.

TABLE 8

| Formulations | Ex 38 | Ex 39 | Ex 40 | Ex 41 | Ex 42 |
|---|---|---|---|---|---|
| MillBase A | 80.35 | — | — | — | — |
| MillBase B | — | 80.35 | — | — | — |
| MillBase C | — | — | 82.27 | — | — |
| MillBase D | — | — | — | 81.5 | — |
| MillBase E | — | — | — | — | 128.69 |
| CYMEL ™ 303 | 30 | 30 | 26.67 | 26.67 | 50 |
| Polyesterdiol Ex. 8 | 9.98 | — | — | — | — |
| Polyesterdiol Ex. 14 | — | 9.98 | — | — | — |
| PED 55-225 | — | — | 14.29 | — | — |
| PED 33-225 | — | — | — | 13.89 | — |
| Hardener A | — | — | — | — | 12.05 |
| DC-57 | 1.33 | 1.33 | 1.33 | 1.33 | 2.00 |
| Nacure ™ 2500 | 0.8 | 0.8 | 0.8 | 0.8 | 1.20 |

The formulations were further diluted with the solvent blend to provide a Zahn cup #3 viscosity of 20 seconds.

The NVM and VOC content of the formulations at the adjusted viscosity were as follows:

| | Ex. 38 | Ex. 39 | Ex. 40 | Ex. 41 | Ex. 42 |
|---|---|---|---|---|---|
| NVM % | 85.4 | 86.85 | 83.57 | 84.89 | 82.25 |
| VOC | 1.82 | 1.71 | 2.00 | 1.92 | 2.17 |

The formulations were applied to Bonderite™ panels and baked 20 minutes at 300° F. Properties are shown in Table 9.

TABLE 9

| | Gloss | | Knoop | Pencil | MEK | Direct |
|---|---|---|---|---|---|---|
| | 20° | 60° | Hardness | Hardness | RUBS | Impact |
| Ex 38 | 41 | 79 | 5.4 | 2H | >300 | 120 |
| Ex 39 | 47 | 82 | 5.8 | 2H | >300 | 110 |

TABLE 9-continued

|  | Gloss | | Knoop | Pencil | MEK | Direct |
|---|---|---|---|---|---|---|
|  | 20° | 60° | Hardness | Hardness | RUBS | Impact |
| Ex 40 | 32 | 76 | — | B | >300 | 150 |
| Ex 41 | 41 | 81 | — | B | >300 | 166 |
| Ex 42 | 81 | 97 | 19.9 | 4H | >300 | 20 |

As is evident from Table 9, coatings with the polyesterdiols of the present invention (Examples 38 and 39) show significantly better properties than is the case with commercial polyesterdiol counterparts (Examples 40 and 41). The coating with 100% Hardener A (Examples 42) demonstrates very high hardness, but a lack of flexibility as evidenced by a Direct Impact value of only 20.

EXAMPLES 43–46

Formulations containing the polyesterdiols of this invention and commercial polyesterdiols and a hardening agent were prepared by blending corresponding ratios of the formulations of each of Examples 38–41 brought to the same viscosity with the formulation of Example 42 containing Hardener A to provide polyesterdiol/hardener A binder ratios of 70:30 (70% binder based on the polyesterdiol and 30% binder based on the hardening agent).

These formulations were applied to Bonderite™ panels and baked 20 minutes at 300° F. Properties are shown in Table 10.

TABLE 10

|  | Gloss | | Knoop | Pencil | MEK | Direct |
|---|---|---|---|---|---|---|
|  | 20° | 60° | Hardness | Hardness | RUBS | Impact |
| Ex 43 (Ex. 8 NPG/ADIP) | 58 | 87 | 13.8 | 4H | >300 | 100 |
| Ex 44 (Ex. 14 PG/ADIP) | 51 | 85 | 10.5 | 3H | >300 | 80 |
| Ex 45 (PED 55-225) | 36 | 79 | 4.6 | F | >300 | >160 |
| Ex 46 (PED 33-225) | 44 | 82 | 4.9 | F | >300 | 120 |

As seen from Table 10, the polyesterdiols of the present invention again demonstrate significantly better properties in combination with a hardening component versus the commercial counterparts. The formulation of Example 43 containing the polyesterdiol of Example 8 demonstrates very high hardness and outstanding flexibility as compared, for example, with Joncryl™ 504, with a VOC of 1.9, which is 1.0 lb/Gal. less than the VOC of the Joncryl™ 504 formulation.

The composition containing the polyesterdiols of the present invention combined with hardening agents can be used as a major component of the binder for high and ultra high solids coating formulations, as well as reactive diluents for other polymer systems providing significant dilution and VOC reduction without a loss in properties and, at the same time, an improvement of some important properties.

As is evident from Table 10, cured films containing both a hardener and the polyesterdiols of this invention (Examples 43 and 44) show significantly better properties vs. the commercial counterparts (Examples 45 and 46).

We have discovered that solvent (unreacted diol) free curable compositions with highly desirable properties can be provided by compositions comprising:

a. Polyesterdiols of present invention having number average molecular weight Mn<700, preferably <600, more preferable <500 and most preferable <400 with polydispersity index Mw/Mn<1.4, preferably <1.35, more preferable <1.3 and most preferable <1.25. The polyesterdiols further characterized as having a non-volatile material (NVM) content in excess of about 96 wt %, preferable >98%, and more preferable >99%, preferably free of catalytic impurities.

b. Amino crosslinking agent being a poly(methylol, alkoxymethyl), preferably a poly(methylol, methoxymethyl) amino crosslinking agent.

The above solvent free curable compositions optionally, but preferably containing:

c. A hardening agent containing functional groups being able to react with B. (amino crosslinking agent), with number average molecular weight<800, preferably <700, more preferable <600, and most preferable <500, being compatible with the component A. and increasing hardness of the curable composition upon crosslinking.

d. A pigment or pigment compositions or pigment-filler composition.

The solvent-free curable composition may also contain small quantities of catalysts accelerating reaction between b., a. and optionally c., as well as other additives usually used to improve specific properties of paint (coating) compositions and films produced from them.

The solvent-free curable compositions of present invention demonstrate strong viscosity reduction with temperature increase and in most cases provide low viscosity acceptable for spraying application even at mild increase in temperature.

The polyesterdiols of the present invention demonstrate unusually strong improvements achievable in the preparation of curable, liquid coating compositions which are essentially organic solvent free, i.e., are coating compositions which are essentially free of organic compounds which generate VOC, including viscosity-adjusting solvents as described above and unreacted diols. By "essentially free" of VOC generating compounds is meant coating formulations which contain less than 3 wt % VOC compounds, preferably less than 2 wt %, more preferably less than 1 wt % and most preferably less than 0.5 wt % of such compounds. Solvent-free liquid compositions of this invention offer numerous advantages. They are flowable at or about room temperature and can be applied to surfaces by conventional liquid coatings techniques, including spray methods at temperatures less than about 250° F., preferably less than about 200° F., and they exhibit significantly reduced flammability (flash point greater than 100° F., preferably greater than 144° F.). Most significantly, since these liquid formulations contain an insignificant amount of organic solvent and unreacted diol, substantially no VOC is generated from solvent or unreacted diol during the coating and baking steps. While some VOC may be generated from product crosslinking, this amount is small compared to prior art compositions containing solvents and/or unreacted diol, as shown below.

The polyesterdiol component used in such solvent-free compositions is a liquid as described above, but having a number average molecular weight (Mn) of less than 700, preferably less than 600, more preferably less than 500 and most preferably less than 400, with a polydispersity index (Mw/Mn) of less than 1.4, preferably less than 1.35, more preferably less than 1.30 and most preferably less than 1.25, and an NVM content in excess of 96 wt %, preferably in excess of 98 wt %, more preferably in excess of 99 wt %, and most preferably about 100 wt %, as described above.

For solvent-free coatings, the preferred crosslinking agents are methylol (alkoxymethyl) amino crosslinking agents containing little or no organic solvents generating VOC where the alkoxy group contains 1 to 4 carbon atoms, preferably 1 to 2 carbon atoms, and most preferably one carbon atom. Although the mixed alkoxy melamines (e.g., 50% methoxy, 50% butoxy) offer the advantage of lower viscosity when used in solvent-born coating formulations ("Resimene®" Amino crosslinker Resins, Monsanto, 1991, pg. 25, Chart 8), the opposite effect was discovered for solvent and/or unreacted diol-free coating compositions of the present invention, where amino crosslinking agents with primarily methoxy as the alkoxy groups demonstrated lower viscosity, lower VOC, better properties, etc.

Therefore, preferable examples of amino crosslinking agents are Cymel™ 300, 301, 303, 303LF, 350, 373, 385, Powderlink 1174, Beetle 65, produced by Cytec, Resimene® AQ7550, 735, 745, 746, 747, 980, 975 from Monsanto. A big advantage of the solvent-free compositions of the present invention is the ability to form stable mixtures with limited but essential amounts of water without using water-miscible solvents or unreacted diols contributing to VOC.

The compositions can contain from about 0.5 up to about 20 wt %, more preferably from about 1 to 10 wt % of added water to further reduce the viscosity of the composition.

The solvent-free composition of this invention without water addition will generally exhibit a Brookfield viscosity at 25° C. of less than 4,000 cps, preferably less than 3,000 cps, more preferably less than 2,000 cps.

A particular advantage of the invention is the large viscosity reduction at higher temperatures. Even at mild temperatures, e.g., 60° C., viscosities of less than 600 cps, preferably less than 500 cps, more preferably less than 400 cps and most preferably less than 300 cps are achievable, which renders them more flowable for application to substrates at higher temperatures, e.g., about 140° F. up to about 175° F., without the attendant fire hazard or explosion risk encountered at these higher temperatures due to the relative absence of inflammable solvents in the composition.

Another particular advantage of the solvent-free curable compositions of the present invention is the ability to imbibe water and achieve a large viscosity reduction both at 25° C. as well as at mildly higher temperatures.

Brookfield viscosities of less than 1000 cps, preferably less than 700 cps, more preferably less than 500 cps, and most preferably less than 400 cps, are achievable at 25° C. with curable water-extended compositions of the present invention.

Brookfield viscosities of less than 200 cps, preferably less than 150 cps, and more preferably less than 100 cps, are achievable at 60° C. with curable water-extended compositions of the present invention.

The above range of viscosities actually covers requirements for any known type of application technology used for liquid coatings, including spray.

The molecular weight of the hardening component is the major factor in their applicability in solvent-free curable compositions of the present invention. In general, lower molecular weight hardening agents provide lower viscosity, higher hardening effect and better compatibility with water, without the addition of water-compatible solvents. The reduction of molecular weight of the hardening agent is limited by volatile components. The preferable hardening agents should have NVM>90 wt %, more preferably >95 wt %, and most preferably >98 wt %.

The preferable weight level of amino crosslinking agent is 50–120% of the stoichiometric amount, more preferably 60–100%, where the stoichiometric amount is calculated as 2 methylol and/or alkoxymethyl group per one aliphatic hydroxyl group and 1.5 times this amount per one phenolic hydroxyl.

One of the important factors affecting the amount VOC of solvent-free curable compositions of the present invention is the level of catalyst. The increase in catalyst causes an increase in VOC formation as well as an increase in hardness of the coating. The increase in hardening agent level provides an increase in hardness with substantially no increase in VOC. Therefore, the balance of catalyst level and hardening agent level provides the means to minimize VOC for any particular hardness requirements (up to 6–7H).

Another important consideration is the difference between VOC measured at standard EPA-defined conditions and VOC formed at actual baking conditions. This phenomena is generally known for any condensation type crosslinking reaction and not specific to solvent-free curable compositions of the present invention. However, the present invention teaches how to optimize one or another for solvent-free compositions.

In particular for a coating with a required hardness, where EPA VOC requirements measured at 230° F. require a reduction in catalyst level or acidity, the required hardness can still be achieved with increased baking conditions, i.e., time and/or temperatures using the compositions of the invention. Baking conditions generate higher VOC than EPA conditions. However, optimization of the invention at EPA conditions is usually not optimal at baking conditions. To achieve better VOC at baking conditions, some increase in catalyst and reduction in bake (temperature, time) are required, but causes some increase in EPA-determined VOC. The increase in hardening agent permits reduction of catalyst and/or baking conditions to reduce both EPA- and baking-VOC.

Examples 47–49 illustrate the preparation of essentially organic solvent-free coating formulations in accordance with this invention.

EXAMPLES 47–49

Millbases having the following composition were prepared as disclosed above:

| Millbase | A | B | C |
|---|---|---|---|
| Polyesterdiol (Ex. 8) | 50.0 | — | — |
| Polyesterdiol (Ex. 14) | — | 50.0 | — |
| PED-55-225 (93.3%) | — | — | 53.6 |
| Wetting Agent (52%) | 1.24 | 1.24 | 1.24 |
| TiO$_2$ (R-706) | 150.0 | 150.0 | 150.0 |

Specific quantities of the above formulated millbases were further let down to provide solvent-free paint formulas as set forth in Table 11.

TABLE 11

| Formulation | Ex. 47 | Ex. 48 | Ex. 49 |
|---|---|---|---|
| Millbase A | 67.08 | — | — |
| Millbase B | — | 67.08 | — |
| Millbase C | — | — | 68.28 |
| Polyesterdiol Ex. 8 | 13.33 | — | — |
| Polyesterdiol Ex. 14 | — | 13.33 | — |
| PED-55-225 | — | — | 14.29 |
| Cymel ™ 300 | 20.0 | 20.0 | 20.0 |
| Dow Corning 57 | 0.115 | 0.115 | 0.115 |

TABLE 11-continued

| Formulation | Ex. 47 | Ex. 48 | Ex. 49 |
|---|---|---|---|
| Brookfield Visc. cps 25° C. | 2860 | 1540 | 4810 |
| Brookfield Visc. cps 60° C. | 324 | 260 | 560 |
| Cymel ™/Binder wt % | 40.0 | 40.0 | 40.0 |

The formulations were further catalyzed at a 0.3% PTSA per binder level by mixing in BYK™-451 and applied to Bonderite™ 1000 (unpolished) panels and baked 20' at 350° F. Properties are shown in Table 12.

TABLE 12

|  | Gloss 20° | Gloss 60° | Knoop Hardness | Pencil Hardness | MEK Rubs | Direct Impact |
|---|---|---|---|---|---|---|
| Ex. 47 | 65.0 | 85.0 | 11.0 | 4H | >300 | 60 |
| Ex. 48 | 66.5 | 87.0 | 9.0 | 4H | >300 | 50 |
| Ex. 49 | 60.0 | 83.0 | 3.5 | F | >300 | 110 |

As is evident from Table 12, solvent-free coatings made using polyesterdiols of the present invention (Ex. 47 and 48) demonstrate significantly better film properties and lower formulation viscosities at both 25° C. and 60° C. than coatings made using a commercial polyesterdiol counterpart (Ex. 49). The formulations of Examples 47 and 48 also provide cured coatings having good Knoop Hardness values while maintaining reasonably good Direct Impact values.

Cured coating formulations having higher hardness values can be prepared by inclusion in the composition of from about 0.5 to about 60 wt %, preferably 2–40 wt %, based on binder content, of a hardening agent which contains at least two hydroxy functional groups per molecule reactive with the amino crosslinking agent and which hardening agent is compatible or miscible with the polyesterdiol component present in the composition and which has a relatively low molecular weight. Preferred hardening agents are those containing phenolic, aromatic, cycloaliphatic and/or aliphatic hydroxy functionality and having an Mn of at least 200 up to about less than 800, preferably less than 700, more preferably less than 600 and most preferably less than 500. Such hardening agents include those described above, including bisphenolic compounds such as Bisphenol-A, Bisphenol-Z and the like; low molecular weight aromatic or cycloaliphatic polyesterdi(poly)ols such as described in U.S. Pat. No. 4,104,240 or U.S. Pat. No. 4,540,771, bis para-hydroxy phenyl benzoates (bis-PHBA esters) of $C_2$ to $C_8$ diols of the type described in U.S. Pat. No. 5,166,289, particularly bis esters of diols such as neopentyl glycol or propane diol and para-hydroxybenzoic acid (PHBA).

Another preferred hardening agent is the phenol-aliphatic functional hardening agent which is the reaction product of PHBA and a glycidyl ester of $C_4$ to $C_{18}$ saturated carboxylic acids, e.g., the reaction product of PHBA and the glycidyl ester of neodecanoic acid, identified above as Hardener A.

The following examples illustrate the preparation of essentially organic solvent-free coating formulations also containing reactive hardening agents.

EXAMPLES 50–57

Millbases having the following compositions were prepared as described above:

| Millbase | A | B |
|---|---|---|
| Polesterdiol (Ex. 14) | 150.0 | — |
| Ped-33-225 (95.2%) | — | 157.26 |
| Wetting Agent (52%) | 3.72 | 3.72 |
| TiO₂ (R-706) | 450.0 | 450.0 |

Specific quantities of the above formulated milo bases were further let down to provide solvent free paint formulations as set forth in Table 13.

TABLE 13

| Formulation | 50 | 51 | 52 | 53 | 54 | 55 | 56 | 57 |
|---|---|---|---|---|---|---|---|---|
| Millbase A | 134.16 | 134.16 | 134.16 | 134.16 | — | — | — | — |
| Millbase B | — | — | — | — | 135.85 | 135.85 | 135.85 | 135.85 |
| Polyesterdiol Ex. 14 | 21.67 | 14.67 | 5.19 | 0.15 | — | — | — | — |
| Polyesterdiol 33-225 | — | — | — | — | 28.01 | 20.80 | 7.96 | 2.69 |
| Hardener A | — | — | 14.98 | 13.02 | — | — | 15.91 | 13.96 |
| Cymel ™ 300 | 45.0 | — | 46.5 | — | 40.0 | — | 43.18 | — |
| *Cymel ™ 1135 | — | 52.0 | — | 53.5 | — | 46.86 | — | 50.14 |
| **Dow 57 25% solution in Butanol | 1.00 | 1.00 | 1.00 | 1.00 | 1.00 | 1.00 | 1.00 | 1.00 |
| PED/Hard Agent Ratio | 100/0 | 100/0 | 72/28 | 72/28 | 100/0 | 100/0 | 72/28 | 72/28 |

*Mixed hexamethoxy/hexabutoxy methyl melamine (from American Cyanamid).
**The solvent in the additive reduces NVM by 0.37%.

The level of amino crosslinking agent in the formulation is based on 2 methoxymethyl (butoxymethyl) groups per one aliphatic hydroxyl and 3 methoxymethyl (butoxymethyl) groups per phenol group.

The formulations were further catalyzed to the 0.15 wt % of PTSA per binder level with BYK™-451, which additionally reduces NVM by 0.33%. (The reduction of NVM caused by solvents in the additive can be avoided by the use of 100% NVM additives, free of solvent diluents).

The catalyzed formulations were used to determine experimental NVM at standard ASTM conditions (1 hour at 230° F.) as well as at baking conditions. For the purpose of evaluation "low bake" 20' at 300° F. and "high bake" 20' at 350° F. were used with the understanding that, for example, 10' at 350° F. would provide some sort of intermediate results.

The catalyzed formulations were also used to determine viscosities and 25° C. and 60° C. as well as film properties after bake at 300° F. and 350° F. (20 minutes).

Properties of the formulations and baked coatings are shown in Table 14.

TABLE 14

| Formulation | 50 | 51 | 52 | 53 | 54 | 55 | 56 | 57 |
|---|---|---|---|---|---|---|---|---|
| Brookfield Vis cps 25° | 1120 | 800 | 2200 | 1300 | 1600 | 1000 | 2800 | 1600 |
| Brookfield Vis cps 60° | 142 | 122 | 216 | 144 | 198 | 152 | 276 | 185 |
| NVM (ASTM D2369-90) | 95.59 | 94.99 | 95.00 | 94.23 | 95.35 | 95.73 | 94.71 | 94.60 |
| Density lb/Gal. | 14.87 | 14.31 | 14.79 | 14.23 | 14.73 | 14.36 | 14.75 | 14.26 |
| VOC (EPA Meth. 24) | 0.66 | 0.72 | 0.74 | 0.82 | 0.68 | 0.61 | 0.78 | 0.77 |
| Bake 20' × 300° F. | | | | | not cured | not cured | | |
| Gloss 20° | 53 | 52 | 61 | 55 | | | 58 | 53 |
| Gloss 60° | 82 | 80 | 85 | 84 | | | 83 | 81 |
| Pencil* Hardness | >2B | >2B | B | >2B | | | >2B | >2B |
| MEK Rubs | >300 | >300 | >300 | >300 | | | >300 | >300 |
| Dir Impact | >160 | >160 | >160 | >160 | | | >160 | >160 |
| NVM 20' × 300° F. | 92.37 | 91.25 | 92.73 | 91.26 | | | 92.97 | 91.95 |
| VOC 20' × 300° F. | 1.13 | 1.25 | 1.08 | 1.24 | | | 1.04 | 1.15 |
| Bake 20' × 350° F. | | | | | | | | |
| Gloss 20° | 36 | 42 | 54 | 44 | 32 | 36 | 48 | 50 |
| Gloss 60° | 77 | 79 | 84 | 81 | 70 | 76 | 82 | 82 |
| Pencil* Hardness | HB | B | 2H | HB | >2B | >2B | F | 2B |
| MEK Rubs | >300 | >300 | >300 | >300 | >300 | >300 | >300 | >300 |
| Dir Impact | 100 | 120 | 100 | 100 | >160 | >160 | 120 | 140 |
| NVM 20' × 350° F. | 90.87 | 88.59 | 90.77 | 88.78 | 90.97 | 89.21 | 90.90 | 89.21 |
| VOC 20' × 350° F. | 1.36 | 1.63 | 1.37 | 1.60 | 1.33 | 1.55 | 1.33 | 1.54 |

Note* The higher the B hardness number, the less hard is the coating; the higher the H hardness number, the harder the coating.

As can be seen from Table 14, the solvent free coating compositions demonstrate very strong reduction of viscosity even at very mild increase in temperature from 25° C. to 60° C. Viscosities at 60° C. fit the requirements for most of the spray equipment used in the coating industry. Even viscosities at 25° C. can be spray applied by the use of more specialized and powerful spray equipment.

VOC contents are very low, although not 0 despite the practical absence of solvents. The partial reaction between the amino crosslinking agents (Cymel™ 300, Cymel™ 1135), the polyesterdiols and the hardening agent is accompanied by the formation of methanol and butanol— byproducts of the crosslinking reaction, which adds to VOC level.

A very strong effect of baking conditions on VOC formation during the crosslinking reaction is also shown in Table 14. VOC formation at 350° F. (20') is actually double the standard VOC corresponding to the EPA definition, while VOC formed at 300° F. (20') is in between.

It is important to note that none of the formulations of Examples 50–57 catalyzed at 0.15% PTSA/binder level produced good film properties at 300° F. bake, even though most of them were completely cured based on MEK-Double Rubs test results. However, at 350° F. (20') bake the formulation of Example 52 based on the blend of polyesterdiol of Example 14 and the hardening agent in a 72/28 ratio provided a good coating with 2H pencil hardness, 100 direct impact, 0.74 standard measured VOC and 1.37 actual baking VOC.

The data in Table 14 also show a significantly higher actual bake VOC for formulations made with methoxybutoxy substituted Cymel™ 1135 versus methoxy substituted Cymel™ 300, especially at 350° F.×20' bake.

Examples 50–57 were repeated as set forth, except that the level of PTSA catalyst mixed in was increased to 0.30 wt %, based on binder weight.

Properties of the formulations and baked coatings prepared therefrom are shown in Table 15.

TABLE 15

| | 50 | 51 | 52 | 53 | 54 | 55 | 56 | 57 |
|---|---|---|---|---|---|---|---|---|
| NVM (ASTM) | 93.00 | 91.44 | 93.10 | 91.52 | 93.43 | 92.43 | 93.16 | 92.02 |
| VOC (EPA) | 1.04 | 1.22 | 1.01 | 1.21 | 1.02 | 1.09 | 1.01 | 1.14 |
| Bake 20' × 300° F. | | | | | | | | |
| Gloss 20° | 69.5 | 35 | 75 | 71 | 62 | 61 | 74.6 | 61.6 |
| Gloss 60° | 86.5 | 74 | 89 | 87.4 | 84.4 | 82.3 | 88.5 | 83.9 |
| Hardness Knoop | 5.9 | 6.5 | 7.4 | 4.1 | <1 | <1 | 3.2 | <1 |
| Hardness Pencil | F | HB | 2H | F | >2B | >2B | HB | B |
| MEK-Rubs | >300 | >300 | >300 | >300 | >300 | >300 | >300 | >300 |
| Direct Impact | 100 | 100 | 80 | 80 | >160 | >160 | 120 | >160 |
| NVM 20' × 300° F. | 91.6 | 89.62 | 91.92 | 89.62 | 92.23 | 90.20 | 92.05 | 90.16 |
| VOC 20' × 300° F. | 1.25 | 1.49 | 1.19 | 1.48 | 1.14 | 1.41 | 1.17 | 1.40 |
| Bake 20' × 350° F. | | | | | | | | |
| Gloss 20° | 60.6 | 41.2 | 68.4 | 61.5 | 47.7 | 43.9 | 69.8 | 60.7 |
| Gloss 60° | 85.5 | 78.3 | 88.8 | 87.3 | 81.3 | 78.1 | 89.5 | 86.6 |
| Hardness Knoop | 14.4 | 11.8 | 23.6 | 19.6 | 4.37 | 5.9 | 12.1 | 9.2 |
| Hardness Pencil | >4H | >4H | >4H | >4H | F | F | >4H | 2H |
| MEK-Rubs | >300 | >300 | >300 | >300 | >300 | >300 | >300 | >300 |
| Direct Impact | 50 | 50 | 40 | 50 | 100 | 100 | 60 | 60 |
| NVM 20' × 350° F. | 89.45 | 86.72 | 89.54 | 86.81 | 89.80 | 86.91 | 90.07 | 86.65 |
| VOC 20' × 350° F. | 1.57 | 1.90 | 1.55 | 1.88 | 1.50 | 1.88 | 1.47 | 1.90 |

*The additional catalyst quantity reduces NVM an additional 0.33% due to the solvent present in the catalyst.

The data from Table 15 shows that catalyst level (0.30 vs. 0.15) has a very strong effect on the generation of VOC. The standard EPA defined VOC increased 0.3–0.4 lb/gal. At bake conditions, VOC is also increased about 0.1 to 0.4 lb/gal. Also, the Table data shows that higher temperature bakes (350° F.) generate more VOC than lower temperature bakes (300° F.).

In general, good balance of formulation viscosity properties, cured film properties and low VOC content are achieved in formulation 52 containing the polyesterdiols of the invention crosslinked using hexamethoxymethylmelamine. The data also show that alkoxy substituents higher than methoxy in the amino crosslinking agent generate a higher VOC content on baking. The data of Table 15 demonstrates that 2H hardness can be achieved with formulation 52 catalyzed to 0.3 PTSA level at "low bake" 300° F.

at 20 minutes conditions. The formulation provides 1.01 lb/gal. EPA standard VOC and 1.19 lb/gal. actual VOC at baking conditions. Comparison with Table 14 shows that lower catalyst level provides lower standard VOC (0.74 lb/gal.) but higher actual VOC at baking conditions (1.37 lb/gal.). Also, the viscosities of the formulations of Examples 50–53 are lower than those formulations containing the polyesterdiol component of the prior art (Examples 54–57). Therefore, a formulation can be optimized depending on which VOC is required.

Solvent-free formulations based on polyesterdiol of the present invention provide significantly better film properties than commercial counterparts at all studied formulations. So, the same film properties can be achieved with polyesterdiols of the present invention at lower catalyst level and/or lower base conditions providing significantly lower VOC. Substitution of part of the polyesterdiol with hardening agent does not affect VOC, but significantly improves film properties.

An unexpected and useful advantage of the present invention is the fact that very low viscosity, solvent free, curable compositions can be achieved by the addition of limited but essential quantities of water to the solvent/diol-free formulations. Table 16 presents data on the effect with respect to viscosity of water addition to the formulation examples 50–57 catalyzed with 0.3% PTSA.

TABLE 16

Viscosities at water addition to the Formulations of Examples 50–57 catalyzed at 0.3 wt % PTSA.

| | Brookfield Visc. (cps) 25° C. | | Brookfield Visc (cps) 60° C. | | | | | |
|---|---|---|---|---|---|---|---|---|
| Water Added (wt %) | | | | | | | | |
| Example | 0 | 2 | 0 | 2 | 4 | 6 | 8 | 10 |
| 50 | 950 | 600 | 127 | 121 | 102 | 81 | 77.5 | 82.5 |
| 51 | 690 | 620 | 101 | 130 | 146 | — | — | — |
| 52 | 1750 | 909 | 203 | 134 | 124 | 94.5 | 100 | 103 |
| 53 | 1050 | 2100 | 139 | 158 | 606 | — | — | — |
| 54 | 1370 | 970 | 186 | 190 | 147 | 140 | — | — |
| 55 | 900 | 2200 | 134 | 244 | 2800 | — | — | — |
| 56 | 2310 | 1200 | 240 | 198 | 180 | 256 | — | — |
| 57 | 1350 | 10K | 190 | 243 | 10K | — | — | — |

The data in Table 16 shows that formulations made using methoxy-butoxy substituted amino crosslinking agent (Cymel™ 1135) demonstrate increase in viscosity with addition of water. (Examples 51, 53, 55, 57) and cause gelation at small addition of water. On the other hand, formulations made using oxy type Cymel™ 300 and the polyesterdiol of the present invention imbibe up to 10% water per formulation (20% water per binder) and demonstrate a very strong viscosity reduction (Examples 50 and 52). An especially strong reduction in viscosity is achieved for blends of the polysterdiol of the present invention containing the hardening agent (Ex. 52).

Formulation 52, when undiluted with water, has significantly higher viscosity then formulation 50 without hardening agent. However, the addition of 6–8% of water significantly reduces viscosity to about the same very low level, (80–90 cps). Also, formulations made with the commercial polyesterdiol and Cymel™ 300 imbibe only up to 4–6% of water and demonstrate significantly less reduction of viscosity with lowest viscosities about 2 times higher (Examples 54 and 56) than formulations containing the polyesterdiols of the present invention.

The data in Table 16 also demonstrates that solvent-free formulations having low viscosities at 60° C. can be achieved, which means that these formulations can be sprayed on surfaces at higher temperatures without fire or explosion hazards attendant with coatings containing volatile organic solvents.

The above results demonstrated outstanding value of blends of polyesterdiols of the present invention and Hardener A as materials for solvent-free curable coating compositions. However, many of the hardening agents are crystalline compounds.

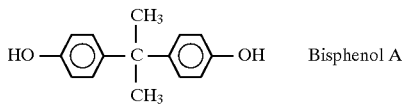 Bisphenol A

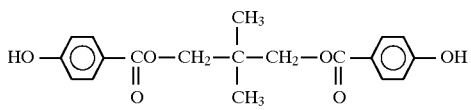

NPG-Bis PHBA ester or non-flowable at ambient condition material

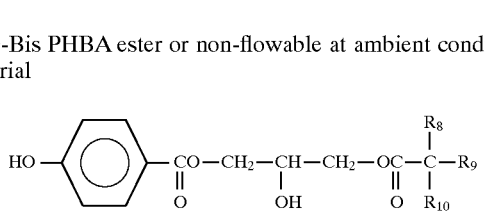

Glydexxe®-PHBA ester (Hardener A).

To demonstrate their compatability with polyesterdiols as well as to prepare convenient flowable ambient condition 100% NVM raw material convenient for industrial application several blends were prepared (Table 17).

TABLE 17

| | Polyesterdiol - Hardening Agent Blends | | | | | | | |
|---|---|---|---|---|---|---|---|---|
| | BL-1 | BL-2 | BL-3 | BL-4 | BL-5 | BL-6 | BL-7 | BL-8* |
| PG Adipate Ex. 14 | 280 | 400 | 400 | 120 | 80 | 15 | 100 | — |
| PG Adipate 33-225 | — | — | — | — | — | — | — | 126 |
| Glydexx ® Hardener A | 120 | — | — | 280 | 320 | 85 | 100 | 280 |
| Bisphenol A | — | — | 100 | — | — | — | — | — |
| NPG- | — | 100 | — | — | — | — | — | — |

TABLE 17-continued

Polyesterdiol - Hardening Agent Blends

|  | BL-1 | BL-2 | BL-3 | BL-4 | BL-5 | BL-6 | BL-7 | BL-8* |
|---|---|---|---|---|---|---|---|---|
| BisPHBA Hard Agent wt % | 30 | 20 | 20 | 70 | 80 | 85 | 50 | — |
| Viscosity 25° C. cps | 1500 | 2050 | 2100 | 18500 | 46000 | 74000 | 4300 | 18900 |
| Viscosity 60° C. cps | 128 | 162 | 167 | 625 | 1060 | 1400 | 257 | 700 |

*Blend 8 had lower NVM due to NVM of Fomrez ™ 32-225 ≈ 95.2%. All the blend demonstrated high stability and were handleable at ambient conditions.

The blends BL-4 to BL-6 are 100% NVM hardening agents flowable at ambient conditions. These blends can be used instead of unflowable Hardener A as reactive hardening diluents in paints curable through amino crosslinking agents (acrylics, alkyds, polyesters, etc.)

The blend BL-7 is a 100% NVM, mildly hardening reactive diluent providing better VOC reduction than blends BL-4 to BL-6.

The blends BL-1, BL-2, and BL-3 are low viscosity, 100% NVM reactive diluents amenable to substitution of significant amounts of binder (up to 50% and more) in commercial solvent based coating compositions without sacrificing essential properties, in many cases with improvement of essential properties, providing strong VOC reduction for such formulations. The blends BL-1, BL-2, and BL-3 are also low viscosity, 100% NVM raw materials for the solvent-free curable compositions of Examples 58–65.

Millbases having the composition shown in Table 17A were prepared as described above:

TABLE 17A

|  | MB-BL-1 | MB-BL-2 | MB-BL-3 | MB-Ex 14 |
|---|---|---|---|---|
| BL-1 | 200 |  |  |  |
| BL-2 |  | 200 |  |  |
| BL-3 |  |  | 200 |  |
| PG Adipate (Ex. 14) |  |  |  | 200 |
| Wetting Agent Disperbyk - 110 (52%) | 5 | 5 | 5 | 5 |
| TiO$_2$ | 500 | 500 | 500 | 500 |

EXAMPLES 58–65

Specific quantities of the millbases shown in Table 17A were further let down to provide solvent-free, catalyst-containing paint formulations as shown in Table 18. The formulations of Examples 58, 60, 62 and 64 contain CYMEL™ 300 crosslinking agent at a conditionally calculated level of 100% stoichiometric which assumes 2 methoxymethyl groups per aliphatic hydroxyl and 3 methoxy methyl groups per 1 phenol group.

This 100% stoichiometry level was used to recalculate how much Cymel™ 300 would constitute 120% of stoichiometry.

TABLE 18

| Formulation Ex. | 58 | 59 | 60 | 61 | 62 | 63 | 64 | 65 |
|---|---|---|---|---|---|---|---|---|
| MB BL-1 | 211.51 | 70.5 | — | — | — | — | — | — |
| MB BL-2 | — | — | 211.51 | 70.5 | — | — | — | — |
| MB BL-3 | — | — | — | — | 141.0 | 70.5 | — | — |
| MB Ex 14 | — | — | — | — | — | — | 211.51 | 70.5 |
| BL-1 | 13.77 | 30.0 | — | — | — | — | — | — |
| BL-2 | — | — | 17.04 | 30.0 | — | — | — | — |
| BL-3 | — | — | — | — | 12.49 | 30.0 | — | — |
| PGAdip. (Ex 14) | — | — | — | — | — | — | 21.33 | 30 |
| Cymel ™ 300 | 76.23 | 0 | 72.96 | 0 | 47.51 | 0 | 68.67 | 0 |
| Dow 57 | 0.30 | 0.10 | 0.30 | 0.10 | 0.20 | 0.10 | 0.30 | 0.10 |
| BYK ™-451 | 1.125 | 0.375 | 1.125 | 0.375 | 0.75 | 0.375 | 1.125 | 0.375 |
| PTSA % per binder | 0.15 | 0.15 | 0.15 | 0.15 | 0.15 | 0.15 | 0.15 | 0.15 |
| Cymel ™ 300 wt % | 50.82 | 0 | 48.64 | 0 | 47.51 | 0 | 45.78 | 0 |
| Stoich. % | 120 | 0 | 120 | 0 | 100 | 0 | 120 | 0 |
| Hard Agent wt % per resin blend | 30 | 30 | 20 | 20 | 20 | 20 | 0 | 0 |

Properties of certain of these formulations and properties of baked films prepared therefrom are shown in Table 19. In certain cases, formulations containing the crosslinking agent (Ex. 58 or 64) and formulations free of crosslinking agent (Ex. 59 or 65) were blended at different ratios to provide varied ratios of crosslinking agent as shown in Table 19. This provides a means to evaluate the effect of crosslinking agent ratio on film properties as well as on rheological properties of the coating.

TABLE 19

Formulations Examples 58, 59, 64, 65 at Variable Cymel ™ 300 level (All MEK-Rubs >300).

| Form Ex. | 58 | 58/59 | 58/59 | 58/59 | 64 | 64/65 | 58 | 58/59 | 58/59 | 58/59 | 64 | 64/65 |
|---|---|---|---|---|---|---|---|---|---|---|---|---|
| Cymel ™ 300 % Stoich | 120 | 100 | 90 | 65 | 120 | 100 | 120 | 100 | 90 | 65 | 120 | 100 |
| PTSA per binder | 0.15 | 0.15 | 0.15 | 0.15 | 0.15 | 0.15 | 0.3 | 0.3 | 0.3 | 0.3 | 0.3 | 0.3 |
| NVM (ASTM) | 95.63 | 95.41 | 95.39 | 95.72 | 96.35 | 96.43 | 94.11 | 93.77 | 93.43 | 93.75 | 93.37 | 93.7 |
| VOC (EPA) | 0.65 | 0.68 | 0.68 | 0.63 | 0.54 | 0.53 | 0.87 | 0.92 | 0.97 | 0.925 | 0.98 | 0.93 |
| Bake 20' × 300° F. | | | | | | | | | | | | |
| Gloss 20° | — | — | — | — | — | — | 72 | 72 | 70 | 70.6 | 66 | 66 |
| Gloss 60° | — | — | — | — | — | — | 88 | 87 | 86 | 85 | 86 | 85 |
| Hard. Knoop | — | — | — | — | — | — | 6.14 | 7.5 | 12.0 | 7.3 | 4.01 | 4.5 |
| Hard Pencil | — | — | — | — | — | — | H | 2H | 3H | 2H | HB | F |
| Dir. Impact | — | — | — | — | — | — | 120 | 100 | 80 | 80 | 120 | 120 |
| NVM | — | — | — | — | — | — | 92.55 | 92.76 | 92.28 | 92.18 | 92.12 | 91.97 |
| VOC | — | — | — | — | — | — | 1.10 | 1.07 | 1.14 | 1.16 | 1.17 | 1.19 |
| Bake 20' × 350° F. | | | | | | | | | | | | |
| Gloss 20° | 47 | 51 | 47 | 48 | 41 | 48 | 63 | 67 | 65 | 61.5 | 53 | 58 |
| Gloss 60° | 81 | 84 | 81 | 80 | 79 | 81 | 88 | 88 | 86 | 83 | 83 | 84 |
| Hard Knoop | 9.4 | 10.4 | 12.0 | 8.6 | 5.4 | 4.9 | 24.6 | 23.6 | 21 | 9.3 | 13.2 | 11.64 |
| Hard Pencil | 2H | 2H | 4H | 2H | F | HB | 4H | 6H | 6H | 2H | 4H | 4H |
| Dir. Impact | 80 | 80 | 80 | 80 | 100 | 120 | 40 | 40 | 50 | 60 | 50 | 60 |
| NVM | 91.31 | 91.47 | 91.28 | 91.36 | 91.36 | 91.22 | 90.68 | 90.41 | 90.17 | 90.11 | 90.23 | 90.53 |
| VOC | 1.29 | 1.24 | 1.29 | 1.26 | 1.28 | 1.30 | 1.38 | 1.42 | 1.45 | 1.46 | 1.45 | 1.40 |

The above data demonstrate that the level of crosslinking agent added to the formulations has practically no effect on VOC measured according to EPA technique or measured at baking conditions. The optimum level of crosslinking agent with respect to hardness values at both baking conditions is about 90% of the stoichiometric 100% level, which corresponds to a crosslinker weight of about 43.7 wt %, based on binder weight. This same optimum level also provided relatively low VOC after baking at 300° F.

Optimization of crosslinking agent provided better mechanical properties (hardness 3H, 4H verses 2H for Example 52 (Tables 14,15) without any detrimental effect on VOC. Therefore, additional hardener and optimization of crosslinking agent permit reduction of catalyst and/or baking conditions, providing reduction in VOC for the solvent-free coatings of the invention.

Formulations free of the hardening agents demonstrate significantly poorer film properties, i.e., formulations 64 and 64/65.

These results show that the levels of crosslinking agent, hardener and catalyst, as well as baking conditions can be varied to provide a wide variety of solvent-free coatings meeting required physical property standards.

Additional formulations based on the formulation of Example 60 and blends of Example 60 and 61 formulations to vary the crosslinker level (each containing NPG-Bis PHBA hardening agent) were prepared. Properties and baked coating properties are shown in Table 20.

TABLE 20

| Form. Ex. | 60 | 60/61 | 60/61 | 60/61 | 60 | 60/61 | 60/61 | 60/61 |
|---|---|---|---|---|---|---|---|---|
| Cymel ™ 300, % Stoich | 120 | 100 | 90 | 65 | 120 | 100 | 90 | 65 |
| PTSA % per binder | 0.15 | 0.15 | 0.15 | 0.15 | 0.3 | 0.3 | 0.3 | 0.3 |
| NVM (ASTM) | 95.32 | 95.64 | 95.01 | 95.08 | 94.05 | 93.62 | 93.53 | 93.39 |
| VOC (EPA) | 0.69 | 0.65 | 0.74 | 0.73 | 0.88 | 0.94 | 0.96 | 0.98 |
| Bake 20' × 300° F. | | | | | | | | |
| Gloss 20° | — | — | — | — | 75 | 72.5 | 73 | 74 |
| Gloss 60° | — | — | — | — | 90 | 89 | 88 | 85 |
| Hardness Knoop | — | — | — | — | 9.11 | 10.26 | 16.4 | 8.1 |
| Hardness Pencil | — | — | — | — | 4H | 4H | >4H | 2H |
| Direct Impact | — | — | — | — | 100 | 100 | 80 | 100 |
| NVM | — | — | — | — | 92.27 | 92.52 | 91.98 | 92.53 |
| Bake 20' × 350° F. | | | | | | | | |
| Gloss 20° | 46 | 57 | 55 | 48 | 66 | 65 | 66 | 70 |
| Gloss 60° | 81 | 85 | 83 | 80 | 90 | 88 | 88 | 88 |
| Hardness Knoop | 16.2 | 15.9 | 13.86 | 8.2 | 28.0 | 23.9 | 20.8 | 7.2 |
| Hardness Pencil | >4H | >4H | >4H | 2H | 7H | 6H | >4H | F |
| Direct Impact | 60 | 80 | 60 | 80 | 40 | 40 | 50 | 60 |
| NVM | 91.28 | 91.58 | 91.11 | 91.54 | 90.32 | 90.71 | 90.20 | 90.22 |
| VOC | 1.29 | 1.28 | 1.32 | 1.25 | 1.43 | 1.37 | 1.45 | 1.45 |

The above data shows that solvent-free compositions made using the NPG-Bis PHBA hardening agents exhibit significant improvement in hardness (both Knoop and pencil) at about the same VOC level and at the same catalyst bake conditions, as evidenced by comparison of the data of Table 20 with the data of Table 19. The data also shows that very good mechanical properties are achieved at low catalyst level/high bake temperatures as well as higher catalyst level/low bake temperatures. By regulation of catalyst level and/or baking conditions, the superior properties can be realized along with lower VOC generation.

The data demonstrated significant superiority of Bisphenol hardening agent NPG-bis PHBA ester versus monophenol functional Hardener A. The superiority in rate of crosslinking mechanical properties, etc., have been achieved without any detrimental effect on VOC and at lower level of hardening agent (20% versus 30%).

Additional formulations based on Example 62 and various blends of Examples 62 and 63 were prepared as shown in Table 21 and properties were evaluated. These formulations all contain bisphenol-A as the hardening component.

TABLE 21

| Form. Ex. | 62 | 62/63 | 62/63 | 62/63 | 62 | 62/63 | 62/63 | 62/63 |
|---|---|---|---|---|---|---|---|---|
| Cymel ™ 300, % Stoich | 100 | 75 | 55 | 44 | 100 | 75 | 55 | 44 |
| PTSA % per binder | 0.15 | 0.15 | 0.15 | 0.15 | 0.3 | 0.3 | 0.3 | 0.3 |
| NVM ASTM | 95.56 | 95.63 | 95.47 | 95.65 | 93.62 | 93.38 | 93.64 | 93.61 |
| VOC EPA | 0.66 | 0.65 | 0.67 | 0.64 | 0.94 | 0.98 | 0.94 | 0.95 |
| Bake 20' × 300° F. | | | | | | | | |
| Gloss 20° | — | — | — | — | 81 | 77 | 74 | 75 |
| Gloss 60° | — | — | — | — | 93 | 90 | 88 | 86 |
| Hardness Knoop | — | — | — | — | 21.25 | 20.2 | 19.4 | 8.7 |
| Hardness Pencil | — | — | — | — | 4H | 4H | 4H | 2H |
| Direct Impact | — | — | — | — | 80 | 60 | 60 | 100 |
| NVM | — | — | — | — | 92.01 | 91.94 | 92.05 | 91.91 |
| VOC | — | — | — | — | 1.18 | 1.19 | 1.18 | 1.20 |
| Bake 20' × 350° F. | | | | | | | | |
| Gloss 20° | 51 | 47 | 47 | 36 | 77 | 76 | 77 | 72 |
| Gloss 60° | 84 | 83 | 82 | 78 | 93 | 91 | 92 | 89 |
| Hardness Knoop | 17.6 | 23.8 | 22.5 | 10.8 | 26.7 | 27.7 | 22.4 | 12.9 |
| Hardness Pencil | 4H | >4H | >4H | 4H | >7H | >7H | 4H | 3H |
| Direct Impact | 80 | 60 | 60 | 60 | 40 | 40 | 50 | 50 |
| NVM | 91.53 | 91.16 | 90.96 | 90.36 | 90.15 | 89.73 | 89.75 | 89.36 |
| VOC | 1.25 | 1.31 | 1.34 | 1.43 | 1.46 | 1.52 | 1.52 | 1.57 |

The data presented in Table 21 demonstrates extremely high hardness even at high catalyst/low bake and low catalyst/high bake conditions. This can be interpreted as a higher rate of crosslinking specific for bisphenol-A as the hardening agent versus para-hydroxybenzoate esters as the hardening agent, as shown in Table 20. This phenomena clearly indicates a possibility of further VOC optimization by the regulation of the catalyst level and/or the baking conditions, i.e., reduction of the baking time at 350° F. bake or reduction of bake temperature at a 20 minute bake time. Standard EPA VOC is practically the same as in all previous formulations and depends only on catalyst level. The same can be said about VOC measured at 300° F. baking conditions. Baking at 350° F. demonstrates sharp increase in actual VOC at low level of amino crosslinking agent (less than 55% of stoichiometric level).

The optimum level of amino crosslinking agent is not as clear as the 90% stoichiometric level of the previous examples, but appears to lie in the 75–100% of stoichiometric amount range.

Solvent free formulations are described in Tables 18–21 and blends thereof containing varied crosslinker levels also demonstrate the ability to imbibe limited amounts of water thereby providing the possibility of further viscosity reduction which facilitates application of these coating formulations by conventional spray methods. Table 22 presents data of the effect on viscosity of water addition to various formulations of this invention.

TABLE 22

Water effect on Viscosities of Solvent - Free curable compositions.

| Form Ex. | 58/59 | 58/59 | 58/59 | 60/61 | 60/61 | 60/61 | 62 | 62/63 | 62/63 |
|---|---|---|---|---|---|---|---|---|---|
| Cymel ™ 300 % Stoich | 100 | 90 | 65 | 100 | 90 | 65 | 100 | 75 | 55 |
| % water added | Viscosity 25° C. (cps) | | | | | | | | |
| 0 | 2200 | 2370 | 2460 | 2900 | 2980 | 3240 | 2560 | 2600 | 2800 |
| 4 | 752 | 656 | 696 | 820 | 788 | 852 | 880 | 780 | 764 |
| 6 | 450 | 462 | 586 | 470 | 634 | 548 | — | — | — |
| 8 | 384 | 378 | 378 | 420 | 402 | 404 | 462 | 442 | 390 |
| 10 | — | — | — | — | — | — | 356 | 332 | 372 |
| | Viscosity 60° C. (cps) | | | | | | | | |
| 0 | 277 | 260 | 270 | 310 | 322 | 321 | 283 | 278 | 285 |
| 4 | 121 | 116 | 125 | 123 | 151 | 144 | 141 | 138 | 124 |
| 6 | 102 | 95 | 103 | 123 | 152 | 127 | — | — | — |
| 8 | 76 | 73 | 79.5 | 116 | 87.5 | 77.5 | 97 | 108 | 95 |
| 10 | — | — | — | — | — | — | 84 | 72.5 | 64.2 |

The data presented in Table 22 shows the following:

1. Solvent-free curable coating compositions of the present invention can imbibe 8–10% by weight (or about 20% per binder) water, causing significant reduction viscosities of the compositions.

2. Variation of Hexamethoxymethyl malamine (Cymel™ 300) level within 55–100% of the stoichiometrically calculated amount does not demonstrate as significant an effect on viscosity as the formulations of Table 16.

3. Bisphenol-Type hardening agents do not cause any detrimental effect on the ability of the compositions to imbibe water and reduce viscosity.

4. Addition of up to 8–10% of water reduces viscosities of the solvent-free curable composition of the present invention 6–7.5 times, providing viscosities at ambient conditions in the range 300–400 cps. Liquid coating compositions with such viscosities can be readily applied by a majority of the techniques developed for application of liquid coatings, including electrostatic spray application.

5. At a very mild heating to 60° C., the viscosities of the solvent-free, water-containing curable compositions can be additionally reduced to the 70–80 cps level. Even without water additions, viscosities of about 260–320 cps can be achieved at 60° C., thus providing solvent-free coatings which can be electrostatically sprayed on surfaces at higher temperatures without fire or explosion hazards attendant with coatings containing volatile organic solvent.

6. Some additional viscosity reduction without use of VOC generating solvents can be achieved by the addition of water mixable acetone (recently delisted from VOC generated compounds). Its addition, especially with increase in water content, obviously provides unlimited viscosity reduction, especially for application at low temperature, if needed.

However, the addition of acetone especially at higher quantities, can be detrimental in causing flash point reduction.

High flash point due to the absence of solvents is one of the major advantages of the solvent-free curable compositions of the present invention.

General Conclusions

1. The present invention provides solvent-free curable compositions without VOC-generating solvents and unreacted diols.

2. The solvent-free curable compositions can provide coatings from very low to very high hardness and can cover a wide range of requirements to different coatings applications.

3. The solvent-free curable compositions can be formulated to provide the best standard VOC as measured at the EPA definition or for actual VOC at the baking conditions.

4. The solvent-free curable compositions do not contain solvents causing inflammability as in prior art compositions.

5. The solvent-free water extended curable compositions of the present invention provide very low viscosity for the solvent-free systems even at ambient conditions.

6. The solvent-free curable compositions of the present invention provide strong viscosity reduction, even at very mild heating.

We claim:

1. A polyesterdiol composition having the average structure:

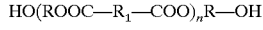

HO(ROOC—R$_1$—COO)$_n$R—OH wherein R is a moiety derived from one or a mixture of aliphatic diols having from 2 to 12 carbon atoms, R$_1$ is a moiety derived from one or a mixture of aliphatic dicarboxylic acids having from 4 to 36 carbon atoms or a mixture of the aliphatic dicarboxylic acid with up to about 50 mol % of an aromatic and/or cycloaliphatic dicarboxylic acid having from 8 to 12 carbon atoms and n a number averaging from greater than 1 to less than 3, the polyester diol composition having a Brookfield viscosity of less than about 3500 cps at about 25° C., a non-volatile material content in excess of about 96 wt %, and a polydispersity of less than about 1.4.

2. The polyesterdiol composition of claim 1 wherein said viscosity ranges from about 300 to about 2000 cps.

3. The polyesterdiol composition of claim 1 wherein the NVM content is in excess of about 98 wt %.

4. The polyesterdiol composition of claim 3 wherein the NVM content is in excess of about 99 wt %.

5. The polyesterdiol composition of claim 1 wherein said acid component consists of one or a mixture of aliphatic dicarboxylic acids having from 4 to 10 carbon atoms.

6. The polyesterdiol composition of claim 1 wherein said aliphatic diol is a branched chain diol having at least one alkyl substituent group at the alpha or beta positions from a hydroxyl group.

7. The polyesterdiol composition of claim 6 wherein said aliphatic diol is a 1,2 or 1,3 diol.

8. The polyesterdiol composition of claim 2 wherein the viscosity ranges from about 300 to less than about 1,000 cps.

9. The polyesterdiol composition of claim 1 having a number average molecular weight in the range of about 250 to 1,000.

10. The polyesterdiol composition of claim 9 having a number average molecular weight in the range of about 250 to 600.

11. The polyesterdiol composition of claim 1 having a polydispersity of less than about 1.25.

12. The polyesterdiol composition of claim 1 which is essentially free of catalytic impurities.

13. A process for producing a polyesterdiol composition having a viscosity of less than about 3500 cps at about 25° C., a non-volatile material content in excess of about 96 wt % and a polydispersity of less than about 1.4 comprising:

(a) heating under esterification conditions and in the absence of added esterification catalyst a mixture comprising: (i) at least one aliphatic dicarboxylic acid or anhydride thereof or a mixture of an aliphatic dicarboxylic acid or anhydride thereof with up to about 50 mol % of an aromatic or cycloaliphatic dicarboxylic acid or anhydride thereof and (ii) at least one aliphatic diol, said diol present at a molar ratio of diol to dicarboxylic acid of at least about 1.5 to 1;

(b) continuing said heating until a polyesterdiol having an acid number of less than about 20 is obtained; and (c) stripping said polyesterdiol at a temperature of less than about 230° C., optionally under vacuum, until a polyesterdiol composition having an NVM content in excess of about 96 wt % is obtained.

14. The process of claim 13 wherein said heating step (b) is continued until an acid number of less than about 10 is obtained.

15. The process of claim 14 wherein said heating step (b) is continued until an acid number of less than about 3 is obtained.

16. The process of claim 13 wherein said stripping step (c) is conducted under vacuum such that a polyesterdiol composition having an NVM content of at least about 98 wt % is obtained.

17. The process of claim 16 wherein a polyesterdiol composition having an NVM content of at least about 99 wt % is obtained.

18. The process of claim 13 wherein the molar ratio of diol to dicarboxylic acid is from about 2:1 to 6:1.

19. The process of claim 18 wherein said molar ratio of from about 2:1 to 4:1.

20. The process of claim 13 wherein said stripping step is conducted under vacuum at a temperature in the range of about 120° to 200° C.

21. A process for producing a polyesterdiol composition having a viscosity of less than about 3500 cps at about 25° C., a non-volatile material content in excess of about 96 wt % and a polydispersity of less than about 1.4 comprising:
(a) heating under esterification conditions and in the presence of catalytic quantities of esterification catalyst a mixture comprising: (i) (A) at least one aliphatic dicarboxylic acid or anhydride thereof or lower alkyl diester thereof, or (B) a mixture of aliphatic dicarboxylic acid or anhydride thereof or lower alkyl diester thereof and up to about 50 mol % of an aromatic or cycloaliphatic dicarboxylic acid or anhydride thereof or lower alkyl diester thereof and (ii) at least one aliphatic diol, said diol present at a molar ratio of diol to dicarboxylic acid or derivative thereof of at least about 1.5 to 1;
(b) continuing said heating until said esterification reaction is substantially complete and an acid number of less than about 20 is achieved;
(c) removing said esterification catalyst from the product of step (b) such that the product contains less than catalytic quantities of said catalyst; and
(d) stripping the product of step (c) by heating at a temperature of less than about 230° C., optionally under vacuum, until a polyesterdiol composition having an NVM content in excess of about 96 wt % is obtained.

22. The process of claim 21 wherein said dicarboxylic acids are in the form of $C_1$ to $C_4$ alkyl dieters and wherein step (b) is conducted until the diester alcohol by-product is essentially liberated and removed by distillation.

23. The process of claim 22 wherein said $C_1$ to $C_4$ alkyl dieters are the dimethyl esters.

24. The process of claim 22 wherein said stripping step (d) is conducted under vacuum such that a polyesterdiol composition having an NVM content of at least about 98 wt % is obtained.

25. The process of claim 22 wherein a polyesterdiol composition having an NVM content of at least about 99 wt % is obtained.

26. The process of claim 21 wherein said dicarboxylic acid component is an aliphatic dicarboxylic acid or acid anhydride or lower dialkyl ester thereof.

27. The process of claim 21 wherein said esterification catalyst is removed by converting the catalyst into a compound insoluble in the product of step (b), followed by separation of the insoluble compound from the product of step (b).

28. The process of claim 21 wherein said stripping step is conducted under vacuum at a temperature in the range of about 120° to 200° C.

29. The process of claim 21 wherein the molar ratio of diol to dicarboxylic acid or derivative thereof is from about 2:1 to 6:1.

30. The process of claim 29 wherein said molar ratio is from about 2:1 to 4:1.

31. The process of claim 21 wherein step (b) is continued until a product having an acid number of less than about 10 is achieved.

32. The process of claim 31 wherein an acid number of less than about 3 is achieved.

33. A polyesterdiol composition prepared by the process of claim 13.

34. A polyesterdiol composition prepared by the process of claim 21.

35. The polyesterdiol composition of claim 1 further containing a phenol functional hardening agent.

36. The polyesterdiol composition of claim 1 further containing a crosslinking agent for said polyester diol composition present in an amount effective to crosslink the composition.

37. The polyesterdiol composition of claim 36 wherein said polyesterdiol is essentially free of catalytic impurities.

38. The polyesterdiol composition of claim 36 wherein said crosslinking agent is a methylol (alkyoxymethyl) amino crosslinking agent.

39. The composition of claim 36 further containing a phenol functional hardening agent present in said composition at a level of from about 1 to 50 wt %, based on the weight of said polyesterdiol and said crosslinking agent.

40. The composition of claim 39 wherein said hardening agent is an ester reaction product of parahydroxybenzoic acid and a glycidyl ester of a tertiary monocarboxylic acid.

41. A polyesterdiol composition having the average structure:

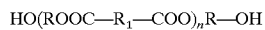

$$HO(ROOC\text{---}R_1\text{---}COO)_nR\text{---}OH$$

wherein R is a moiety derived from one or a mixture of aliphatic diols having from 2 to 12 carbon atoms, $R_1$ is a moiety derived from one or a mixture of aliphatic dicarboxylic acids having from 4 to 36 carbon atoms or a mixture of the aliphatic dicarboxylic acid with up to about 50 mol % of an aromatic and/or cycloaliphatic dicarboxylic acid having from 8 to 12 carbon atoms and n a number averaging from greater than 1 to less than 3, the polyester diol having at least about 75 weight percent of a residual amount of the diols removed therefrom, the polyester diol composition having a number average molecular weight of less than about 600, a Brookfield viscosity of less than about 3500 cps at about 25° C., a non-volatile material content in excess of about 96 weight percent, and a polydispersity of less than about 1.4.

42. The polyester diol composition of claim 41 wherein R is derived from at least one aliphatic diol which has a primary and secondary hydroxyl or at least one diol which has two secondary hydroxyls.

43. The polyester diol composition of claim 41 wherein the polyester diol composition is derived from a reaction mixture of at least of one the aliphatic diols and at least one of the dicarboxylic acids having a ratio of diol to diacid of greater than about 1.5:1 to about 6:1.

44. The polyester diol composition of claim 43 wherein the viscosity ranges from about 300 to less than about 1,000 cps at about 25° C.

45. The polyester diol composition of claim 43 wherein the aliphatic diol is a 1,2 or a 1,3 diol or is a mixture which includes a 1,2 or a 1,3 diol.

46. The polyester diol composition of claim 44 wherein the aliphatic diol is a 1,2 or a 1,3 diol or is a mixture which includes a 1,2 or a 1,3 diol.

47. The polyester diol composition of claim 43 wherein the number average molecular weight is in the range of from about 250 to about 600.

48. The polyester diol composition of claim 44 wherein the number average molecular weight is in the range of from about 250 to about 600.

49. The polyester diol composition of claim 46 wherein the number average molecular weight is in the range of from about 250 to about 600.

50. The polyester diol composition of claim 41 wherein the composition is essentially free of catalytic impurities.

51. A process for producing a polyesterdiol composition having a viscosity of less than about 3500 cps at about 25° C., a non-volatile material content in excess of about 96 wt % and a polydispersity of less than about 1.4 comprising:

(a) heating under esterification conditions and in the absence of an amount esterification catalyst which would be effective for catalyzing a transesterification reaction in a mixture comprising: (i) at least one aliphatic dicarboxylic acid or anhydride thereof or a mixture of an aliphatic dicarboxylic acid or anhydride thereof with up to about 50 mol % of an aromatic or cycloaliphatic dicarboxylic acid or anhydride thereof and (ii) at least one aliphatic diol, the diol present at a molar ratio of diol to dicarboxylic acid of at least about 1.5 to 1;

(b) continuing the heating until a polyesterdiol having an acid number of less than about 20 is obtained; and (c) stripping the polyesterdiol at a temperature of less than about 230° C., optionally under vacuum, until at least about 75 weight percent of a residual amount of the aliphatic diols are removed from the polyester diol and a polyesterdiol composition having a number average molecular weight of less than about 600 and an NVM content in excess of about 96 weight percent is obtained.

52. The process of claim 51 wherein the heating step (b) is continued until an acid number of less than 10 is obtained.

53. The process of claim 51 wherein the heating step (b) is continued until an acid number of less than 3 is obtained.

54. The process of claim 51 wherein the stripping step (c) is conducted under vacuum such that a polyesterdiol having an NVM content of at least about 98 weight percent is obtained.

55. The process of claim 51 wherein a polyesterdiol having an NVM content of at least about 99 wt % is obtained.

56. The process of claim 51 wherein the molar ratio of diol to dicarboxylic acid is from about 2:1 to 6:1.

57. The process of claim 51 wherein the stripping step is conducted under vacuum at a temperature in the range of about 120° to 200° C.

58. The process of claim 51 wherein the polyester diol composition has a viscosity of from about 300 to less than about 1,000 cps at about 25° C.

59. The process of claim 51 wherein at least two different diols are used.

60. The process of claim 51 wherein at least two different diacids are used.

61. The process of claim 51 wherein the dial is a 1,2 or 1,3 dial or a mixture of diols which includes a 1,2 or 1,3 diol.

62. The process as recited in claim 51 wherein the product is stripped with a hot gas.

63. The process as recited in claim 62 wherein the hot gas is steam.

64. A process for producing a polyesterdiol composition having a viscosity of less than about 3500 cps at about 25° C., a non-volatile material content in excess of about 96 wt % and a polydispersity of less than about 1.4 comprising:

(a) heating under esterification conditions and in the presence of catalytic quantities of esterification catalyst a reaction mixture comprising: (i) (A) at least one aliphatic dicarboxylic acid or anhydride thereof or lower alkyl diester thereof, or (B) a mixture of aliphatic dicarboxylic acid or anhydride thereof or lower alkyl diester thereof and up to about 50 mol % of an aromatic or cycloaliphatic dicarboxylic acid or anhydride thereof or lower alkyl diester thereof and (ii) at least one aliphatic diol, said diol present at a molar ratio of diol to dicarboxylic acid or derivative thereof of at least about 1.5 to 1;

(b) continuing the heating until said esterification reaction is substantially complete and an acid number of less than about 20 is achieved;

(c) removing the esterification catalyst from the product of step (b) such that the product contains less catalyst which would be effective for catalyzing a transesterification reaction; and (d) stripping the product of step (c) by heating at a temperature of less than about 230° C., optionally under vacuum, until at least about 75 weight percent of a residual amount of the aliphatic diols are removed from the polyester diol and a polyesterdiol composition having a number average molecular weight of less than about 600 and a NVM content in excess of about 96 wt % is obtained.

65. The process of claim 64 wherein said dicarboxylic acids are in the form of $C_1$ to $C_4$ alkyl diesters and wherein step (b) is conducted until a diester alcohol by-product is essentially liberated and removed by distillation.

66. The process of claim 65 wherein said $C_1$ to $C_4$ alkyl diesters are the dimethyl esters.

67. The process of claim 65 wherein said stripping step (d) is conducted under vacuum such that a polyesterdiol composition having an NVM content of at least about 98 wt % is obtained.

68. The process of claim 65 wherein a polyesterdiol composition having an NVM content of at least about 99 wt % is obtained.

69. The process of claim 64 wherein said dicarboxylic acid component is an aliphatic dicarboxylic acid or acid anhydride or lower dialkyl ester thereof.

70. The process of claim 64 wherein said esterification catalyst is removed by converting the catalyst into a compound insoluble in the product of step (b), followed by separation of the insoluble compound from the product of step (b).

71. The process of claim 64 wherein said stripping step is conducted under vacuum at a temperature in the range of about 120° C. to 200° C.

72. The process of claim 64 wherein the polyester diol composition has a viscosity of from about 300 to less than about 1,000 cps at about 25° C.

73. The process of claim 64 wherein at least two different diols are in the reaction mixture.

74. The process of claim 64 wherein at least two different diacids are in the reaction mixtures.

75. The process of claim 64 wherein the diol is a 1,2 or 1,3 diol or a mixture of diols which includes a 1,2 or 1,3 diol.

76. The process as recited in claim 64 wherein the product is stripped with a hot gas.

77. The process as recited in claim 63 wherein the hot gas is steam.

78. A polyester diol composition made in accordance with the process of claim 51.

79. A polyester diol composition made in accordance with claim 58.

80. A polyester diol composition made in accordance with claim 61.

81. A polyester diol composition made in accordance with claim 64.

82. A polyester diol composition made in accordance with claim 72.

83. A polyester diol composition as recited in claim 41 wherein the polyester diol is stripped with a hot gas to remove the residual amount of the diols and dicarboxylic acids and provide the polyester diol composition with a non-volatile material content in excess of about 96 weight percent.

84. A polyester diol composition as recited in claim 83 wherein the hot gas is steam.

* * * * *